US009575203B2

(12) United States Patent
Chen et al.

(10) Patent No.: US 9,575,203 B2
(45) Date of Patent: Feb. 21, 2017

(54) METHOD FOR MEASURING ROCK WETTABILITY

(75) Inventors: Quan Chen, Sunbury on Thames (GB); Ian Ralph Collins, Sunbury on Thames (GB)

(73) Assignee: BP EXPLORATION OPERATING COMPANY LIMITED, Middlesex (GB)

( * ) Notice: Subject to any disclaimer, the term of this patent is extended or adjusted under 35 U.S.C. 154(b) by 1155 days.

(21) Appl. No.: 13/513,963

(22) PCT Filed: Nov. 19, 2010

(86) PCT No.: PCT/GB2010/002142
§ 371 (c)(1),
(2), (4) Date: Jun. 5, 2012

(87) PCT Pub. No.: WO2011/073608
PCT Pub. Date: Jun. 23, 2011

(65) Prior Publication Data
US 2012/0241149 A1 Sep. 27, 2012

(30) Foreign Application Priority Data

Dec. 16, 2009 (EP) .................................. 09252811
May 6, 2010 (GB) .................................. 1007694.1

(51) Int. Cl.
*G01V 3/32* (2006.01)
(52) U.S. Cl.
CPC .................................. *G01V 3/32* (2013.01)

(58) Field of Classification Search
USPC ... 324/300–322; 600/410–435; 382/128–132
See application file for complete search history.

(56) References Cited

U.S. PATENT DOCUMENTS

| | | | | | |
|---|---|---|---|---|---|
| 3,213,356 | A | * | 10/1965 | Brown | ..................... G01V 3/32 324/303 |
| 3,213,357 | A | * | 10/1965 | Brown | ..................... G01V 3/32 324/303 |
| 3,821,232 | A | * | 6/1974 | Redmore | ............. C07F 9/5535 252/389.22 |
| 3,923,490 | A | * | 12/1975 | Redmore | ................. C07F 9/58 504/153 |

(Continued)

OTHER PUBLICATIONS

Hsu, Wen-Fu., et al; "Wettability of Porous Media by NMR Relaxation Methods"; *Society of Petroleum Engineers, SPE 24761*; pp. 1027-1037 (1992) XP002582762.

(Continued)

*Primary Examiner* — Melissa Koval
*Assistant Examiner* — Tiffany Fetzner
(74) *Attorney, Agent, or Firm* — Conley Rose, P.C.

(57) ABSTRACT method of comparing a secondary oil recovery process with a tertiary oil recovery process, the secondary oil recovery process and the tertiary oil recovery process being applied to a substantially fluid-saturated porous medium containing an oil phase and an aqueous phase. The method comprising using relaxation time measurements in the calculation of a wettability index modification factor for the oil phase or the aqueous phase, thereby comparing the tertiary oil recovery process with the secondary oil recovery process.

18 Claims, 15 Drawing Sheets

(56) References Cited

U.S. PATENT DOCUMENTS

| | | | | |
|---|---|---|---|---|
| 3,965,264 | A * | 6/1976 | Redmore | C02F 1/50 |
| | | | | 514/80 |
| 3,997,293 | A * | 12/1976 | Redmore | C07F 9/58 |
| | | | | 252/389.22 |
| 3,998,833 | A * | 12/1976 | Redmore | C07F 9/58 |
| | | | | 252/389.22 |
| 4,089,650 | A * | 5/1978 | Redmore | C02F 1/50 |
| | | | | 252/389.22 |
| 5,162,733 | A | 11/1992 | Baldwin | |
| 8,278,922 | B2 * | 10/2012 | Hurlimann | G01N 24/081 |
| | | | | 324/303 |
| 8,362,767 | B2 * | 1/2013 | Hurlimann | G01N 24/081 |
| | | | | 324/303 |
| 9,133,709 | B2 * | 9/2015 | Huh | E21B 47/1015 |
| 9,140,117 | B2 * | 9/2015 | de Prisco | G06T 17/05 |
| 9,201,158 | B2 * | 12/2015 | Freed | G01N 24/081 |
| 9,244,188 | B2 * | 1/2016 | Sun | G01V 3/14 |
| 2004/0000905 | A1 | 1/2004 | Freedman et al. | |
| 2006/0116828 | A1 | 6/2006 | Chen et al. | |
| 2006/0132131 | A1 * | 6/2006 | Fleury | G01N 15/0826 |
| | | | | 324/307 |
| 2010/0237860 | A1 * | 9/2010 | Hurlimann | G01N 24/081 |
| | | | | 324/303 |
| 2011/0181277 | A1 * | 7/2011 | Korb | G01N 24/08 |
| | | | | 324/303 |
| 2011/0198078 | A1 * | 8/2011 | Harrigan | E21B 49/008 |
| | | | | 166/254.2 |
| 2011/0306525 | A1 * | 12/2011 | Lighthelm | C09K 8/58 |
| | | | | 507/225 |
| 2012/0229135 | A1 * | 9/2012 | Hurlimann | G01N 24/081 |
| | | | | 324/303 |
| 2012/0241149 | A1 * | 9/2012 | Chen | G01V 3/32 |
| | | | | 166/250.01 |
| 2013/0091941 | A1 * | 4/2013 | Huh | E21B 47/1015 |
| | | | | 73/152.08 |
| 2013/0125630 | A1 * | 5/2013 | Collins | E21B 43/20 |
| | | | | 73/64.56 |
| 2013/0187648 | A1 * | 7/2013 | Freed | G01N 24/081 |
| | | | | 324/303 |
| 2014/0019053 | A1 * | 1/2014 | de Prisco | G06T 17/05 |
| | | | | 702/12 |
| 2014/0035574 | A1 * | 2/2014 | Sun | G01V 3/14 |
| | | | | 324/303 |
| 2015/0015250 | A1 * | 1/2015 | Gzara | G01V 3/32 |
| | | | | 324/303 |

OTHER PUBLICATIONS

Looyestijn, W., et al; "Wettability Index Determination by Nuclear Magnetic Resonance"; *Society of Petroleum Engineers, SPE 93624*; pp. 1-8 (2005) XP002582763.

Freedman, R., et al; "Wettability, Saturation, and Viscosity Using the Magnetic Resonance Fluid Characterization Method and New Diffusion-Editing Pulse Sequences"; *Society of Petroleum Engineers, SPE Proceedings, SPE77397*; pp. 613-625 (2002) XP9060685.

"Improved Method for Measuring Surface Relaxivity"; *Unn Højgaard a Lad, Rogaland Research*; Jostein Kolnes, University of Stavanger; OlaKetil Siqveland, University of Stavanger; Aksel Hiorth, Rogaland Research and Svein M. Skjaeveland, University of Stavanger.

Chen, Q., et al; Quantitative magnetic resonance imaging methods for core analysis, *Geological Society Special Publication*, vol. 267, pp. 193-207 (2006).

"Improved Method for Measuring Surface Relaxivity"; *Unn Høgaard a Lad, Rogaland Research*; Jostein Kolnes, University of Stavanger; Ola Ketil Siqveland, University of Stavanger; Aksel Hiorth, Rogaland Research and Svein M. Skjaeveland, University of Stavanger; SCA2005-48; This paper was prepared for presentation at the International Symposium of the Society of Core Analysis held in Toronto, Canada, Aug. 21-25, 2005; pp. 1/13-13/13.

PCT Notification Concerning Transmittal of International Preliminary Report on Patentability (IPRP); PCT/GB2010/002142, (13 pgs) dated Jun. 28, 2012.

* cited by examiner

METHOD FOR MEASURING ROCK WETTABILITY

This application is the U.S. national phase of International Application No. PCT/GB2010/002124 filed 19 Nov. 2010 which designated the U.S. and claims priority to European Application No. 09252811.6 filed 16 Dec. 2009, and British Application No. 1007694.1 filed 6 May 2010, the entire contents of each of which are hereby incorporated by reference.

The present invention relates to the measurement of wettability. In particular, the present invention relates to the measurement of wettability characteristics and/or changes therein of a porous medium having contained therein a fluid, e.g. a mixed-phase fluid comprising two or more phases, at least one of which is a liquid.

BACKGROUND OF THE INVENTION

In the oil and gas industry, gaining an understanding of the wettability characteristics or wetting condition of a hydrocarbon-bearing, subsurface formation (a "reservoir") may be particularly advantageous. For instance, this understanding may help in the optimisation of field development, since wettability may have an effect on reserve calculation and/or the dynamic behaviour of a reservoir.

Wettability may be defined as the tendency of one fluid to spread on or adhere to a solid surface in the presence of other immiscible fluids.

Thus, for example, wettability may describe the relative preference of a rock to be covered by a certain phase, e.g. water or oil. For example, a rock may be said to be water-wet if the rock has a much greater affinity for water than for oil. Thus, in the case of a water-wet porous rock containing water and oil phases within its pores, substantially all of the internal surface of the pores would be covered with a layer of water. In this case, the water may be termed the "wetting phase".

Conversely, in the case of an oil-wet porous rock, substantially all of the internal surface of the pores would be covered with a layer of oil. In this case, the oil may be termed the "wetting phase".

Similarly, a porous rock of mixed wettability may contain some pores which are water-wet and some which are oil-wet. Also, some regions of an individual pore may be water-wet, while others are oil-wet.

In practice, it will be appreciated that extreme water-wetness or oil-wetness is rare in oil-bearing reservoirs.

It should be appreciated, however, that for a two-phase fluid within a porous rock, the wetting phase will cover more pore surface area and have a stronger surface affinity with the pore walls than the non-wetting phase.

In fluid systems comprising a gaseous phase, e.g. gas-liquid systems, it may be safely assumed that gas is not the wetting phase.

The wettability of a porous rock will depend on the type of rock and will also be affected by any minerals present within the pores. For instance, clean sandstone or quartz may be extremely water-wet, while most rock formations of oil-bearing reservoirs typically may be of mixed-wettability. For a reservoir, wettability alteration from the original water wetting state to a mixed wetting state may have occurred after crude oil migrated into a reservoir trap and reduced the water saturation of the reservoir down to the connate water saturation over geological time. The reservoir wettability depends on crude oil composition, connate water chemistry, and mineralogy of the rock surface, as well as temperature, and pressure and saturation history of the reservoir. The initial fluid saturation distribution in an oil-bearing formation is dependent on the equilibrium between capillary forces and gravity forces at the reservoir scale and at the pore scale. The wetting state can vary with pore and pore-throat geometry. During the oil migration process, gravity is insufficient to overcome the large capillary pressure within micropores, and thus typically micropores remain fully connate water saturated, therefore retaining their original water-wet state. While large pores are often invaded by oil, a connate water film on the rock surfaces of the large pores usually remains. The wettability alteration within the large pores depends on the stability of this water film. In extreme conditions, the water film may be stable and fully coats the surface area of the large pores thereby keeping the oil phase from having direct contact with the pore surface. Thus over geological time, the large pores remain water-wet. Alternatively, the entire surface of the large pores may become coated by the oil phase such that the large pores are oil-wet. Typically, the large pore surfaces are partially in contact with both the water phase and the oil phase, and therefore have mixed-wetting characteristics.

Traditionally, wettability has been characterised in the laboratory using either the Amott or US Bureau of Mines (USBM) indices. However, the methods by which these indices are usually determined are intrusive and are very time consuming. Moreover, they cannot be readily transferred to the field.

It is known that nuclear magnetic resonance (NMR) techniques may be used to ascertain information regarding fluids contained within a porous medium. Advantageously, using NMR techniques offers a non-intrusive means for determining in-situ wettability of fluids in reservoir rocks, i.e., the NMR measurement process does not interfere with the fluid distribution within the pores of the rock. Hence, NMR techniques may be applied to monitor ongoing dynamic processes comprising wettability alteration, such as, ageing and secondary or tertiary oil recovery processes.

Proton ($^1$H) NMR techniques may be particularly well suited for studies of fluids containing water and hydrocarbon phases, e.g. water and oil, within a porous medium.

NMR spectroscopy may be used to measure the spin-lattice (longitudinal) relaxation time ($T_1$) and/or the spin-spin (transverse) relaxation time ($T_2$) of the fluid. For instance, proton ($^1$H) NMR spectroscopy measures the relaxation time for protons within the fluid. From these measurements it may be possible to elucidate certain information concerning the fluid and/or the porous medium.

For instance, core samples may be taken for subsequent analysis using land-based NMR equipment.

Alternatively, NMR logging tools may advantageously be deployed downhole. Such tools typically employ so-called low field spectroscopy.

However, NMR logging tools also suffer from certain drawbacks. For instance, they cannot be used in wellbores or sections thereof which are lined with metal casing. Also, current tools typically can only obtain information in the near-wellbore region, e.g. typically within a radial distance of about 4 inches (10 cm) from the wellbore. It is envisaged, however, that future generations of NMR logging tools may be able to obtain information relating to regions further from the wellbore.

Oil may be produced from a reservoir in a variety of stages, which may be classified as primary, secondary and tertiary stages.

In a primary oil recovery stage, the natural energy of the reservoir is sufficient to produce oil without any assistance.

However only around 10 to 15 percent of the original oil in place of a reservoir is recovered during primary recovery.

In some reservoirs, however, the natural reservoir pressure may not be sufficient to drive oil unaided up a production well to the surface. Therefore, it may be necessary to artificially boost oil production. In this regard, it is known that oil production from a reservoir may be assisted by injection of immiscible fluids, such as water or gas, into the reservoir so as to maintain reservoir pressure, and/or to displace oil towards a production well. Injection of such immiscible fluids generally produces about 20 to 40 percent of the original oil in place.

Where the fluid is unmodified, typically seawater or other readily available water, this process may be classified as being a secondary oil recovery process (alternatively a secondary mode process). In general, such a secondary oil recovery process may be referred to as a water flood or water flooding.

Where the fluid has been treated in some way to modify its properties, this process may be classified as being a tertiary oil recovery process. For instance, tertiary recovery processes may include low salinity water flooding in which a source water such as seawater is treated to reduce its salinity prior to injection into the reservoir and processes in which the to-be-injected fluid comprises one or more specially chosen additives, e.g. chemicals and/or microbes. By appropriately modifying the injection fluid, tertiary oil recovery processes may be used to boost oil production from and/or extend the production life of a reservoir. Typically, tertiary oil recovery processes may displace oil from a reservoir which is not displaced by secondary oil recovery processes. Tertiary recovery processes may often be referred to as enhanced oil recovery (EOR) processes. The EOR techniques offer prospects for ultimate recovery of 30 to 60 percent, or more, of original oil in place.

During the production life of a reservoir different methods of oil recovery may be employed. For instance, initially the reservoir may be produced by a primary recovery method. However, after a while, the reservoir pressure may fall and it may become necessary to utilise secondary oil recovery processes. A period of secondary oil recovery may be followed by one of the EOR processes, in order to maximise production from the reservoir. Of course, the person skilled in the art will appreciate that other sequences are possible: for instance, it may be the case that the reservoir is never produced in primary recovery because the natural reservoir pressure is not high enough; alternatively or additionally, a period of EOR may be applied just after primary recovery, with this EOR process being referred to as a secondary mode EOR process. In contrast, an EOR process may be carried out after the completion of a secondary oil recovery process, with this EOR process being referred to as a tertiary mode EOR process.

SUMMARY OF THE INVENTION

It is a non-exclusive object of the present invention to provide an improved method for determining the wettability of a fluid-saturated porous medium such as a reservoir rock having oil and water phases present within its pores.

It is another non-exclusive object of the present invention to provide a method for determining changes in wettability characteristics of a reservoir, in particular before, during and/or after a secondary or tertiary oil recovery process.

According to a first aspect of the present invention there is provided a method of comparing a secondary oil recovery process with a tertiary oil recovery process, the secondary oil recovery process and the tertiary oil recovery process being applied to a substantially fluid-saturated porous medium containing an oil phase and an aqueous phase, the method comprising:
  (a) providing a first sample of the porous medium, the sample having within the pores thereof a known initial volume of the oil phase;
  (b) measuring a relaxation time for the fluid within the first sample;
  (c) subjecting the first sample to the secondary oil recovery process;
  (d) measuring a relaxation time for the fluid remaining within the first sample after the secondary oil recovery process;
  (e) providing a second sample of the porous medium, the second sample having within the pores thereof a substantially similar known initial volume of the oil phase;
  (f) measuring a relaxation time for the fluid within the second sample;
  (g) subjecting the second sample to the tertiary oil recovery process or, subsequent to step (d) and without carrying out steps (e) and (f), subjecting the first sample to the tertiary oil recovery process;
  (h) measuring a relaxation time for the fluid remaining within the second sample or first sample after the tertiary oil recovery process; and
  (i) using the relaxation time measurements in the calculation of a wettability index modification factor for the oil phase or the aqueous phase, thereby comparing the tertiary oil recovery process with the secondary oil recovery process.

The method may be carried out at ambient conditions in a laboratory. Alternatively, the method may be carried out under reservoir conditions or a laboratory simulation thereof.

The porous medium may be a rock, preferably a rock from a hydrocarbon-bearing formation (a reservoir rock) or a replica thereof. Typical reservoir rocks include sedimentary rocks such as clastic sedimentary rocks and carbonates.

The or each sample of the porous medium may be a plug taken from a core sample. Preferably, where a plurality of plugs is used, the plugs may be drilled in close proximity from the core sample and are therefore expected to have similar rock properties. Such plugs are referred to as "sister plugs".

Alternatively, the or each sample may have been artificially prepared in a laboratory, e.g. the or each sample may comprise a sandpack.

The aqueous phase may comprise brine, fresh water, brackish water or seawater. Preferably, the aqueous phase may be substantially similar in composition to a formation water associated with a reservoir. A suitable aqueous phase may be prepared in the laboratory. Thus, the aqueous phase may comprise a brine solution, which may comprise a formation water or a synthetic formation water.

Where the porous medium is a rock taken from a reservoir that is under primary recovery, the formation water may be connate water i.e. the original water in place in the formation. Connate water may contain a wide range of total dissolved solids (TDS), e.g. from around 100 ppm to 100000 ppm, say around 35000 ppm. Where the rock is taken from a reservoir that is under secondary recovery, the formation water may comprise a mixture of connate water and water that has been injected into the reservoir during secondary recovery, e.g. seawater, brackish water, an aquifer water, surface water such as river or lake water, or a produced water. Typically, seawater may have a TDS-content in the region of 35000 ppm.

The oil phase may comprise live crude oil, stock tank oil (often called "dead" crude oil) and kerosene or other refined oils.

The secondary oil recovery process may comprise a water flood experiment and/or an imbibition experiment. The water flood and/or imbibition experiment may utilise a brine solution. Typically, the brine solution may comprise seawater, brackish water, an aquifer water, a surface water, a produced water, a connate water, a formation water or laboratory-prepared replicas thereof.

The tertiary oil recovery processes may comprise: a low salinity water flood; injection of a fluid containing one or more specially selected agents or additives, e.g. microbes, chemicals, e.g. polymers, alkalis or surfactants; or thermal methods, e.g. hot water or steam injection, or in-situ combustion; or gas injection, e.g. miscible/immiscible gases such as carbon dioxide, hydrocarbon gas or nitrogen gas.

In a low salinity water flood, an aqueous solution is injected into the porous medium, wherein the aqueous solution is of a selected total dissolved solids (TDS) content and/or selected multivalent cation content. Typically, the selected TDS content may be less than 10000 ppm, preferably less than 8000 ppm, for example in the range of 500 to 5000 ppm. Advantageously, the to-be-injected aqueous solution (the "injection water") may be selected to have a lower multivalent cation content than the aqueous phase (the "resident phase") that is contained in the porous medium. For example, the ratio of the multivalent cation content of the injection water to the multivalent cation content of the resident phase is preferably less than 0.9, more preferably, less than 0.8, in particular, less than 0.5.

Where the tertiary oil recovery process comprises injection of a fluid containing one or more specially selected agents or additives, the fluid may comprise an aqueous solution, in which the or each of the agents or additives may be present in a concentration of less than 10000 ppm, e.g. in the range of from 100 to 6000 ppm, preferably from 200 to 5000 ppm.

Suitable microbes may include bacillus, clostridia, pseudomonas, hydrocarbon degrading bacteria, and denitrifying bacteria.

Suitable chemicals may include polymers, surfactants, alkaline materials, or a combination of thereof.

Preferably, the relaxation time measurements may be made using NMR spectroscopy.

Preferably, the relaxation time may be a spin-spin (transverse) relaxation time ($T_2$). Alternatively, the relaxation time may be a spin-lattice (longitudinal) relaxation time ($T_1$).

Preferably, the method may comprise the step of normalizing the measurements by reference to measurements obtained from a porous sample, which sample may be saturated with a single phase, e.g. with water or oil.

Preferably, the method may comprise taking reference or calibration relaxation time measurements for bulk samples of the aqueous phase and/or the oil phase.

In a second aspect of the invention there is provided a method of assessing a change in the wettability of a porous and permeable hydrocarbon-bearing formation in the region surrounding a wellbore that penetrates the formation, the method comprising:

(i) locating an NMR well logging tool within the wellbore at a depth corresponding with an interval of the hydrocarbon-bearing formation;

(ii) measuring a relaxation time for the fluid located within the hydrocarbon-bearing formation;
(iii) optionally, removing the NMR well logging tool from the wellbore;
(iv) injecting a secondary or a tertiary recovery process fluid or an EOR process fluid for a period of time such that a known pore volume or fractional pore volume of the fluid is injected;
(v) optionally shutting in the well for a period of time;
(vi) returning the well back to production and producing and optionally recovering the injected fluids;
(vii) after the injected fluids have been produced, if necessary, re-locating the NMR well logging tool within the wellbore at substantially the same depth as before; and
(viii) measuring a relaxation time for the fluid located within the hydrocarbon-bearing formation.
(ix) optionally repeating steps number (iv) to (viii) with a different recovery fluid to that used in step (iv) originally.

Preferably, the method may be repeated on one or more occasions to measure changes in the wettability characteristics of the formation, e.g. before, during and/or after secondary and/or tertiary oil recovery processes.

Typically, the method of this second aspect of the present invention may be carried out in an injection well, a production well, a test well and/or a newly drilled well.

Optionally, the method of this second aspect of the present invention may be combined with a Single Well Chemical Tracer Test, SWCT test that is designed to measure the in-situ oil saturation (residual oil saturation) after the implemented secondary recovery, tertiary recovery, or EOR process.

When the method of this second aspect of the present invention is combined with a SWCTT, the method is modified by using an aqueous fluid as the injection fluid. The aqueous injection fluid is divided into a first (minor) portion and a second (major) portion. The first portion of the aqueous injection fluid is labelled with a reactive chemical tracer, for example, an ester such as ethyl acetate, that reacts with water during the shut-in period to form a product tracer (for example, an alcohol such as ethanol) that is virtually insoluble in the oil phase that is present in the pores of the formation. Optionally, both the first and second portions of the aqueous injection fluid are labelled with a non-reactive, non-partitioning (material balance) tracer, for example, isopropanol. The amount of the second portion of aqueous injection fluid that is used in step (iv) is typically sufficient to push the first portion of the aqueous injection fluid to a radial distance of at least 5 feet, for example, between 5 to 15 feet from the wellbore. Shutting-in the well in step (v) is essential in order to allow a detectable (measurable) amount of product tracer to form. Typically, the well is shut-in for a period of from one to ten days. Typically, the conversion of the reactive tracer to the product tracer (for example, ester to alcohol conversion) is from 10 to 50%. After, the shut-in period, the well is back-produced and the produced fluid is periodically sampled and immediately analyzed for the content of unreacted ester tracer (e.g. ethyl acetate), the product alcohol tracer (e.g. ethanol) and the optional material balance tracer (e.g. isopropanol). At the start of the back-production step (vi), the unreacted ester tracer and the product alcohol tracer are superimposed at the location that is a radial distance of at least 5 feet from the wellbore. Partitioning of the unreacted ester tracer between the immobile residual oil phase and the mobile water phase delays production of the ester by an increment of volume directly related to the residual oil saturation. The product alcohol tracer, however, is not delayed, and flows back to the well at very nearly the same rate as the water. Since the alcohol does not spend time in the stationary oil phase, it is produced earlier than the unreacted ester tracer (e.g. ethyl acetate), resulting in a separation between the peak concentrations of the product alcohol tracer and unreacted ester tracer. The residual oil saturation is then calculated using the amount of separation between the ester tracer and the alcohol product tracer. Thus, SWCT test results for formations having high residual oil saturations show a large separation between the product alcohol tracer and the reactive ester tracer while test results for formations having low residual oil saturations show a small separation between the product alcohol tracer and the reactive ester tracer. The optional material balance tracer allows for interpretation of the test results in the event that all of the ester tracer reacts, or if some of the ester is stripped away from the produced aqueous fluid by gas breaking out of the fluid or by gas used during gas-lift operations. The change in wettability index determined using the relaxation time measurements determined in step (viii) may be correlated with the residual oil saturation as determined during the SWCT test.

SWCT tests are described in more detail in, for example, Deans, H. A., and Carlisle, C. T.: "Single-Well Tracer Tests in Complex Pore Systems", paper SPE/DOE 14886, presented at the Fifth Symposium on EOR Tulsa, Apr. 20_23, 1986).

In a third aspect of the invention there is provided a method of assessing a change in the wettability of a porous and permeable hydrocarbon-bearing formation in the region surrounding a new wellbore that penetrates the formation, the change being owing, at least in part, to ingress of drilling mud into the formation, the method comprising:
(i) locating a pre-existing wellbore penetrating the hydrocarbon-bearing formation or a similar formation;
(ii) locating an NMR well logging tool within the pre-existing wellbore at a depth corresponding with a portion of the hydrocarbon-bearing formation;
(iii) measuring a relaxation time for the fluid located within the near wellbore region surrounding the pre-existing wellbore;
(iv) drilling a new wellbore at a new location removed from the pre-existing wellbore, whereby the new wellbore penetrates the hydrocarbon-bearing formation;
(v) locating an NMR well logging tool within the new wellbore at a depth corresponding with a portion of the hydrocarbon-bearing formation;
(vi) measuring a relaxation time for the fluid located within the near wellbore region surrounding the new wellbore; and
(vii) comparing the relaxation time measurements from steps (iii) and (vi) to assess the change in the wettability of the fluid in the near wellbore region surrounding the new wellbore, the change being owing, at least in part, to the ingress of drilling mud into the formation during drilling of the new wellbore.

The NMR well logging tool may be a wireline or logging while drilling tool.

Typically, the pre-existing wellbore is a hydrocarbon production wellbore that has been placed on production such that hydrocarbon fluids are present in the near wellbore region of the wellbore.

A plurality of new wellbores may be drilled, each using drilling muds, e.g. oil-based drilling muds, having different compositions, e.g. containing surfactants and/or other additives, in order to compare the effect of the drilling muds on the wettability of the formation.

Once enough field data has been obtained, it may be possible to select a more appropriate drilling mud for each subsequently drilled new well.

In a fourth aspect of the invention there is provided a method of tracking the ageing of a sample of a fluid-saturated porous medium, wherein the fluid is located within the pore structure of the porous medium and the fluid comprises at least two immiscible components or phases, at least one of which is a liquid, the method comprising:
(i) taking a first measurement of a relaxation time distribution of the fluid within the porous medium;
(ii) taking a second measurement of the relaxation time distribution of the fluid within the porous medium after an interval of time;
(iii) taking one or more further measurements of the relaxation time distribution of the fluid within the porous medium at subsequent intervals of time until the relaxation time distribution is substantially unchanged from one measurement to the next, thereby indicating that the sample is aged completely or at least to an acceptable extent.

Preferably, the two components or phases may comprise an aqueous phase and an oil phase.

The sample of porous medium may be a core sample, e.g. taken from a rock such as a reservoir rock or the like. Alternatively, it may be a sandpack or the like which has been specially prepared, typically in a laboratory.

The measurements of the relaxation time may be carried out at regular or irregular intervals over a period of time. The number, frequency and regularity of the measurements that are taken as well as the period during which they are taken may depend on a great many factors, including the nature of the porous medium and the composition of the fluid. For example, the relaxation time measurements may be made once a day or once every few days.

Preferably, the relaxation time may be measured using an NMR spectrometer.

Preferably, the relaxation time may be a transverse (spin-spin) relaxation time.

After ageing, the sample of porous medium may be used in further tests or experiments.

According to another aspect of the present invention there is provided a method of determining wettability distribution characteristics at both pore and field scales of a reservoir, i.e., wettability is determined as functions of both pore size and height above a free water level at a reservoir.

In a further aspect of the invention there is provided a computer-implemented method for determining wettability characteristics of a fluid-bearing porous medium, the method comprising the steps of:
receiving measurement data indicative of a relaxation time of fluid present in the porous medium at a defined fluid saturation;
receiving reference data indicative of one or more reference relaxation times of the fluid; and
calculating a wettability index on the basis of differences between the received measurement data and the received reference data, said wettability index being indicative of the wettability characteristics of the porous medium at the defined fluid saturation.

The method may further comprise receiving a plurality of measurement data, each of which is indicative of a relaxation time of fluid present in the porous medium:
i) at different points in time;
ii) at different locations in the porous medium; or iii) at different stages before, after and/or during at least one of a primary, secondary or tertiary fluid recovery process;

calculating the wettability index for each of the plurality of measurement data, respectively; and calculating, on the basis of a comparison of the calculated wettability indices, a wettability index modification factor indicative of a change in the wettability characteristics of the porous medium.

The method for determining wettability characteristics defined above decouples certain factors (such as fluid saturation and microscopic distribution, pore structure, rock mineralogy, and distribution of paramagnetic impurities, on the pore surface, as well as the crude oil composition) from an NMR relaxation time distribution, and includes both the surface coverage and surface affinity factors for the wettability index and the wettability index modification factor.

This method can also evaluate surface coverage and surface affinity contribution to wettability separately.

Advantageously, the wettability index modification factor can be used to evaluate wettability alteration of enhanced oil recovery processes by comparing surface coverage and surface affinity of a secondary oil recovery process with that of a tertiary oil recovery process.

The method may further comprise the step of receiving parameter data indicative of parameters relating to pore size, capillary pressure, fluid saturation of the porous medium and/or height above free water level in the porous medium, in order to calculate the wettability index as a function of the parameters.

The different locations in the porous medium referred to above may relate to first and second wellbores arranged to penetrate the porous medium, the wettability index modification factor calculated being indicative of a change between the wettability characteristics of the porous medium at the first and second wellbores.

The fluid present in the porous medium may comprise at least two immiscible fluid components or phases, and the wettability index can be calculated for at least one of said fluid components or phases.

The reference data may comprise one or more of relaxation time measurements made on:
i) a sample of the porous medium that is saturated with a single aqueous phase;
ii) a sample of the porous medium that is saturated with a single oil phase; and/or
iii) bulk samples of an aqueous phase and/or an oil phase corresponding to that of the porous medium.

A mixed-wettability NMR signature after water flood has been identified in applying the method for determining wettability characteristics defined above. This signature is characterized by the relaxation time ($T_2$) peak value after a water flood is larger than any relaxation time ($T_2$) component of bulk crude oil and a fully water saturated core plug, but less than the relaxation time of bulk water. This mixed-wettability NMR signature can be employed to identify mixed-wettability characteristics in a porous medium comprising multiple fluid components or phases.

The method may further comprise normalising the measurement data based on the reference data.

The relaxation time measurements may be spin-spin (transverse) relaxation time measurements made using NMR spectroscopy.

The porous medium may comprise a reservoir rock formation, a sample thereof or a replica thereof.

In accordance with the above aspect the invention further provides a system for determining wettability characteristics of a fluid-bearing porous medium, the system comprising:

data receiving means arranged to receive measurement data indicative of a relaxation time of fluid present in the porous medium at a defined fluid saturation;

data receiving means arranged to receive reference data indicative of one or more reference relaxation times of the fluid; and computer-implemented means arranged to calculate a wettability index on the basis of differences between the received measurement data and the received reference data, said wettability index being indicative of the wettability characteristics of the porous medium at the defined fluid saturation.

The system may further comprise:

data receiving means arranged to receive a plurality of measurement data, each of which is indicative of a relaxation time of fluid present in the porous medium:
i) at different points in time;
ii) at different locations in the porous medium; or
iii) at different stages before, after and/or during at least one of a primary, secondary or tertiary fluid recovery process;

computer-implemented means arranged to calculate the wettability index for each of the plurality of measurement data, respectively; and computer-implemented means arranged to calculate, on the basis of a comparison of the calculated wettability indices, a wettability index modification factor indicative of a change in the wettability characteristics of the porous medium.

BRIEF DESCRIPTION OF THE DRAWINGS

In order that the invention may be more fully understood, it will now be described by way of example only and with reference to the accompanying drawings in which:

FIG. 1-2 shows the initial water saturation (Swi) distribution as a function of pore size (r) at different capillary pressures, calculated using a cylindrical pore throat and spherical pore body model.

FIG. 1-3 shows the initial water saturation (Swi) distribution as a function of relaxation time at different capillary pressures, calculated using a cylindrical pore throat and spherical pore body model.

FIG. 1-4 shows the water volume distribution as a function of pore size (r) at 100% water saturation (Sw=1) and at initial water saturation (Swi=0.2) for core plug No. 156 at a capillary pressure of 182 psi, calculated using a cylindrical pore throat and spherical pore body model.

FIG. 1-5 shows the initial oil volume distribution as a function of pore size (r) at initial oil saturation (Soi=0.2) for core plug No. 156 at a capillary pressure of 182 psi, calculated using a cylindrical pore throat and spherical pore body model.

FIG. 1-6 shows the water volume distribution as a function of pore size (r) at 100% water saturation (Sw=1) and at initial water saturation (Swi=0.2) for core plug No. 157 at a capillary pressure of 182 psi, calculated using a cylindrical pore throat and spherical pore body model.

FIG. 1-7 shows the initial oil volume distribution as a function of pore size (r) at initial oil saturation (Soi=0.2) for core plug No. 157 at a capillary pressure of 182 psi, calculated using a cylindrical pore throat and spherical pore body model.

FIG. 1-8 shows the initial oil saturation as a function of pore size (r) at a capillary pressure of 182 psi corresponding to an overall initial oil saturation of 0.8 for sister plugs Nos. 156 and 157, calculated using a cylindrical pore throat and spherical pore body model.

FIG. 1-9 shows the $T_2$ relaxation time distributions for a bulk crude oil and for a core plug (No. 156) at different fluid saturation conditions.

FIG. 1-10 shows $T_2$ relaxation time distributions for a bulk crude oil and for core plug No. 157 at different fluid saturation conditions;

FIG. 1-11 shows the wettability index of the oil phase as a function of pore size (r) after ageing at initial oil saturation at a capillary pressure of 182 psi for core plug No. 156.

FIG. 1-12 shows the wettability index of the oil phase as a function of pore size (r) after ageing at initial oil saturation at a capillary pressure of 182 psi for core plug No. 157.

FIG. 2-1 shows the $T_2$ relaxation time distributions of sister core plugs after water flooding with three different salinity brines.

FIG. 3-1 shows initial water saturation (Swi) as a function of $T_2$ relaxation time for MEOR core plugs at a capillary pressure of 100 psi.

FIG. 3-2 shows initial water saturation (Swi) as a function of pore-body radius (r) for MEOR core plugs at a capillary pressure of 100 psi.

FIG. 3-3 shows water volume distribution as a function of pore-body radius (r) at 100% water saturated conditions (Sw=1) and at initial water saturation (Swi=0.28).

FIG. 3-4 shows $T_2$ relaxation time distributions for a bulk crude oil and for core plugs at different fluid saturation conditions for an MEOR core plug experiment.

FIG. 4-1 shows an experimental set-up for a first sandpack sample undergoing brine imbibition alongside a second sandpack sample undergoing microbial enhanced oil recovery (MEOR);

FIG. 4-2 shows $T_2$ distributions for brine imbibition experiments conducted on the first sandpack;

FIG. 4-3 shows $T_2$ distributions for MEOR experiments conducted on the second sandpack;

FIG. 4-4 is a graph comparing $T_2$ distributions for the first sandpack after brine imbibition and the second sandpack after MEOR;

FIG. 4-5 is a graph showing oil recovery with time from the first sandpack and the second sandpack;

FIG. 4-6 shows T2 distributions for a 100% brine saturated sandpack, a 100% inoculum saturated sandpack, and the inoculum saturated sandpack after ageing for six days.

FIG. 5 shows a method of using NMR spectroscopy primary, secondary, and tertiary oil recovery process comparisons via a modified wettability index.

FIG. 6 shows a method of determining a porous medium wettability from NMR spectroscopy relaxation and wettability index modification information.

DETAILED DESCRIPTION OF THE INVENTION

Figure 1:
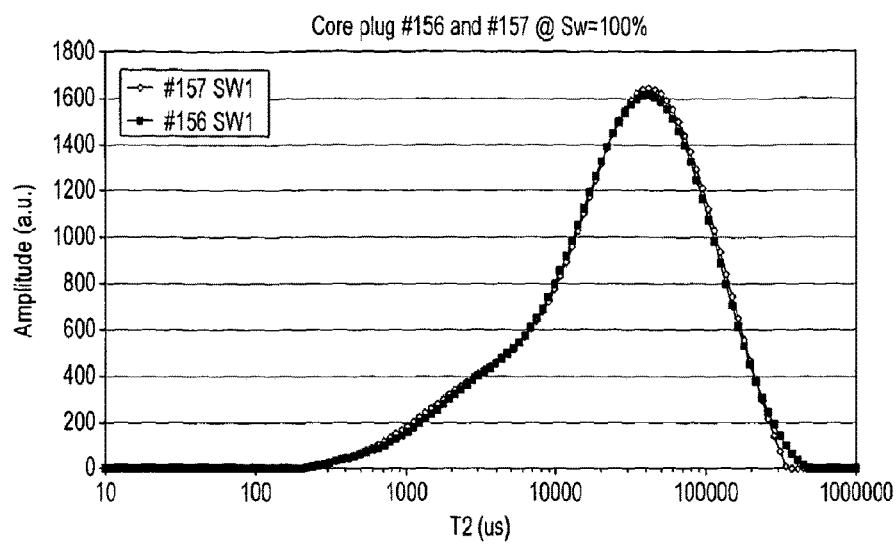
FIG. 1-1 shows the $T_2$ relaxation time distributions of core plugs No. 156 and No. 157 at 100% water saturation.

A fluid-saturated pore within a rock may be divided into two regions, namely a surface region and a bulk region. The surface region comprises a relatively thin layer, e.g. having a thickness of no more than a few molecules, over the internal surface of the pore. The bulk region comprises the remainder of the internal volume of the pore.

It has been found that, typically, the relaxation time for a molecule in the surface region is considerably less than for a molecule within the bulk region. Without wishing to be bound by any theory, this may be due to the effect on molecules within the surface region of paramagnetic centres within the pore walls. In the case of proton ($^1$H) NMR spectroscopy, it may also be due in part to reduced rotational speed of the hydrogen protons at the rock surface.

In porous reservoir rocks, the pores are typically less than about 100 μm in diameter. Accordingly, the bulk region may occupy a relatively small proportion of an individual pore.

The spin-spin relaxation time for a fluid in a pore may be affected by contributions from three relaxation mechanisms: (i) relaxation of the fluid in the bulk region; (ii) relaxation of the fluid in the surface region; and (iii) relaxation owing to self diffusion of the fluid in the gradient of the applied magnetic field. Generally, it may be difficult to separate the relative contributions of the three mechanisms, particularly when the fluid contains more than one phase, e.g. an aqueous phase and an oil phase.

For a fluid-saturated medium in the case where low field NMR spectroscopy with a short echo time is used, e.g. as may typically be used in oilfield NMR logging, it may be assumed that the contribution to spin-spin relaxation time owing to self diffusion may be negligible, since molecular diffusion in internal magnetic field gradients may be negligible.

Hence, for a 100% water-saturated porous medium (at $S_w=1$), the inverse of the spin-spin relaxation time ($T_2$) of the water phase in a pore in the fast-diffusion limit may be expressed as:

$$\frac{1}{T_{2,W1}} = \rho_{2,W}\frac{A}{V} + \frac{1}{T_{2B,W}} \quad (1)$$

In equation (1), $T_{2,W1}$ is the spin-spin relaxation time of fully water saturated rock, $\rho_{2,w}$ is the spin-spin relaxivity of the water phase, $T_{2B,W}$ is the bulk spin-spin relaxation time of the water phase, A is the surface area of the pores within the porous medium and V is the pore volume.

The water phase typically comprises connate water, formation water, or the like.

In the case of a 100% water-saturated porous rock, Equation (1) may often be approximated by neglecting the bulk relaxation term. This may be done, since the relaxation time of water within porous rock of a reservoir is much shorter than the relaxation time of bulk water. Therefore:

$$\frac{1}{T_{2,W1}} = \rho_{2,W}\frac{A}{V} \quad (2)$$

The V/A ratio can be used to measure pore size by the following equation:

$$\rho_{2,W}T_{2,W}=V/A=r/k \quad (3)$$

where k is a geometrical constant, which depends on pore shape and is equal to 1, 2, and 3 for flat pores or fractures, cylindrical pores, and spherical pores, respectively, and r is half of the pore aperture for flat pores or fractures and is the pore body radius for cylindrical or spherical pores.

For a pore-body and pore-throat throat model of a porous medium, a pore body-to-throat ratio (BTR) may be defined as:

$$BTR = \frac{r}{R} \qquad (4)$$

where r is the radius of a pore body which is connected to another pore body by a pore throat with radius of R.

BTR can be determined for example by comparing the pore throat size distribution determined by mercury injection experiments and pore body size distribution determined by NMR DDIF (Decay due to Diffusion in Internal Field) or by analyzing thin-sections of rock samples using electron microscopy.

The NMR CPMG (Carr-Purcell-Meiboom-Gill) pulse sequence is the most common method for measuring the $T_2$ relaxation time. The pulse sequence consists of a 90° pulse followed by a series of "m" 180° pulses to generate an echo after each 180° pulse, which forms a train of "m" echoes as a result (where "m" is an integer). The time interval between adjacent 180° pulses is the echo time, TE.

For a simple bulk fluid like water, the echo amplitude decays as a single-exponential function of the echo time as given by $$M(mTE) = M(0)\exp(-mTE/T_{2B,W}) \qquad (5)$$

where M(mTE) is the transverse magnetization, and M(0) is the signal amplitude that corresponds to the initial transverse magnetization.

A fluid (e.g. water) bearing porous medium is typically comprised of a wide distribution of pore sizes. Consequently, the total NMR signal is the sum of the signals from fluids within all the individual pores of the porous medium. It can be expressed as a multi-exponential decay in a CPMG measurement of transverse magnetization:

$$M(mTE) = \sum_{i=1}^{n} A_i \exp\left(-\frac{mTE}{T_{2,i}}\right) \qquad (6)$$

where $A_i$ is the signal amplitude of the ith component with characteristic relaxation time $T_{2,i}$.

An inverse Laplace transform of data following Equation (6) will yield the $T_2$ relaxation time distribution. At a fast diffusion limit and weak diffusion coupling regime, the $T_2$ distribution can be linearly converted to a pore-size distribution by Equation (3).

The sum of the signal amplitude ($A_i$) of all (n) components is equal to the signal amplitude of the initial transverse magnetization as stated in Equation (7):

$$\sum_{i=1}^{n} A_i = M(0) \qquad (7)$$

The signal amplitude ($A_i$) is directly proportional to pore-volume fraction of the ith component with relaxation time of $T_{2,i}$.

A core analysis process often starts from cleaning reservoir core plugs with solvent to a strongly water-wet state. During a primary drainage process (to mimic crude oil migration) such as a drainage capillary pressure experiment in a laboratory, an initially fully water saturated core plug is de-saturated by air or oil using either porous plate or centrifugal techniques. For instance when using the porous plate technique with air or nitrogen gas displacing water, after a displacement pressure has been applied and the pressure has equilibrated to fix the capillary pressure (Pc), the remaining water saturation can be determined by measuring the amount of water produced from the core plug. If the applied pressure exceeds the threshold pressure of a given pore, the air or nitrogen gas will invade the pore and occupy the centre of the pore with the remaining water coating the surface of the pore as a layer. The pores will remain fully water saturated if the applied pressure does not exceed the threshold pressures of the pores. According to the Young-Laplace equation for the water-air or water-nitrogen system with zero contact angle, the relationship between capillary pressure ($P_c$) and a threshold cylindrical pore throat radius ($R_t$) which remains fully water saturated is given by $$P_C = \frac{2\sigma}{R_t} \qquad (8)$$

where σ is interfacial tension or surface tension which is 72 mN/m for the air-water system.

In an oil-bearing reservoir, the primary drainage capillary pressure curve governs the initial water and oil saturation above the oil-water contact. During the oil migration process, the capillary pressure is balanced by gravitational forces arising from the density difference between water and oil at the equilibrium condition. Accordingly, the fluid distribution as a function of height above the free water level (H) is:

$$P_C = (\rho_w - \rho_o)gH \qquad (9)$$

where $P_c$ is capillary pressure, $\rho_w$ and $\rho_o$ are the densities of the water phase and oil phase in a reservoir, respectively, g is the gravitational acceleration, and H is the height above free water level in the reservoir.

According to Equations (4) and (3), at the threshold capillary pressure, the corresponding maximum fully water saturated pore body radius ($r_t$) and the threshold spin-spin relaxation time $T_{2,t}$ of the water phase are related to the threshold pore throat radius ($R_t$) by $$r_t = R_t BTR \qquad (10)$$

$$T_{2,t} = \frac{R_t BTR}{k\rho_{2,w}} \qquad (11)$$

During de-saturation of a water phase by a non-wetting phase (gas or oil), the pore bodies will remain fully water saturated if the applied pressure does not exceed the threshold capillary pressures of the pore bodies. If the applied pressure exceeds the threshold capillary pressure of a given pore body, the non-wetting phase will invade the pore body through a connected pore throat and will occupy the centre of the pore body with remaining water phase forming a coating on the surface of the pore wall. At the threshold capillary pressure, it is assumed that the thickness of the layer of the remaining water phase in the non-wetting phase (air or oil) invaded pore bodies is equal to the threshold pore throat radius of $R_t$. For calculating initial water saturation during de-saturation processes, the pore body and pore throat model also assumes that the volume of pore throats is negligible in comparison with the volume of the pore bodies.

Therefore, during a de-saturation process the initial water saturation, $S_{wi}$, as a function of the pore body radius (r), capillary pressure ($P_c$) and pore shape factor (k) can be determined by:

$$S_{wi}(r, P_C, k) = 1 - \left(\frac{r - 2\sigma/P_C}{r}\right)^k \text{ if } r > r_t; \quad (12a)$$

$$\text{or } S_{wi} = 1 \text{ if } r \leq r_t.$$

where, as discussed above, k is equal to 1, 2, and 3 for flat pores or fractures, cylindrical pores, and spherical pores, respectively. The physical boundary condition of $S_{wi}$ is $0 < S_{wi} \leq 1$.

For a two-phase system with water and oil, the initial oil saturation ($S_{Oi}$) as a function of the pore body radius (r), capillary pressure ($P_c$), and pore shape factor (k) can be determined by:

$$S_{Oi}(r, P_C, k) = \left(\frac{r - 2\sigma/P_C}{r}\right)^k \text{ if } r > r_t; \quad (12b)$$

$$\text{or } S_{Oi} = 0 \text{ if } r \leq r_t$$

Substituting Equations (3) and (11) into Equation (12a) gives the initial water saturation, $S_{wi}$, as a function of spin-spin relaxation time, $T_{2,W1}$, capillary pressure ($P_c$) and pore shape factor (k), for fully water saturated pore bodies:

$$S_{wi}(T_{2,W1}, P_C, k) = 1 - \left(\frac{T_{2,W1} - \frac{2\sigma}{k\rho_{2,w}P_C}}{T_{2,W1}}\right)^k \quad (13a)$$

$$\text{if } T_{2,W1} > T_{2t}; \text{ or } S_{wi} = 1 \text{ if } T_2 \leq T_{2t}$$

For a two-phase system with water and oil, the initial oil saturation, $S_{Oi}$, as a function of the spin-spin relaxation time ($T_{2,W1}$), capillary pressure ($P_c$) and pore shape factor (k) can be determined by $$S_{Oi}(T_{2,W1}, P_C, k) = \left(\frac{T_{2,W1} - \frac{2\sigma}{k\rho_{2,w}P_C}}{T_{2,W1}}\right)^k \quad (13b)$$

$$\text{if } T_{2,W1} > T_{2t}; \text{ or } S_{Oi} = 0 \text{ if } T_{2,W1} \leq T_{2t}$$

As an example, for a spherical pore shape model, where k=3, equations (12a), (12b), (13a) and (13b) can be simplified as Equations (14a), (14b), (15a) and (15b), respectively:

$$S_{wi}(r) = 1 - \left(\frac{r - r_t/BTR}{r}\right)^3 \text{ if } r > r_t; \quad (14a)$$

$$\text{or } S_{wi} = 1 \text{ if } r \leq r_t.$$

$$S_{Oi}(r) = \left(\frac{r - r_t/BTR}{r}\right)^3 \text{ if } r > r_t; \quad (14b)$$

$$\text{or } S_{Oi} = 0 \text{ if } r \leq r_t.$$

$$S_{wi}(T_{2,W1}) = 1 - \left(\frac{T_{2,W1} - T_{2t}/BTR}{T_{2,W1}}\right)^3 \text{ if } T > T2t; \quad (15a)$$

$$\text{or } S_{wi} = 1 \text{ if } T2 \leq T2t.$$

$$S_{Oi}(T_{2,W1}) = \left(\frac{T_{2,W1} - T_{2t}/BTR}{T_{2,W1}}\right)^3 \text{ if } T_{2,W1} > T_{2t}; \quad (15b)$$

$$\text{or } S_{Oi} = 0 \text{ if } T_{2,W1} \leq T_{2t}$$

Figures 1, 2:
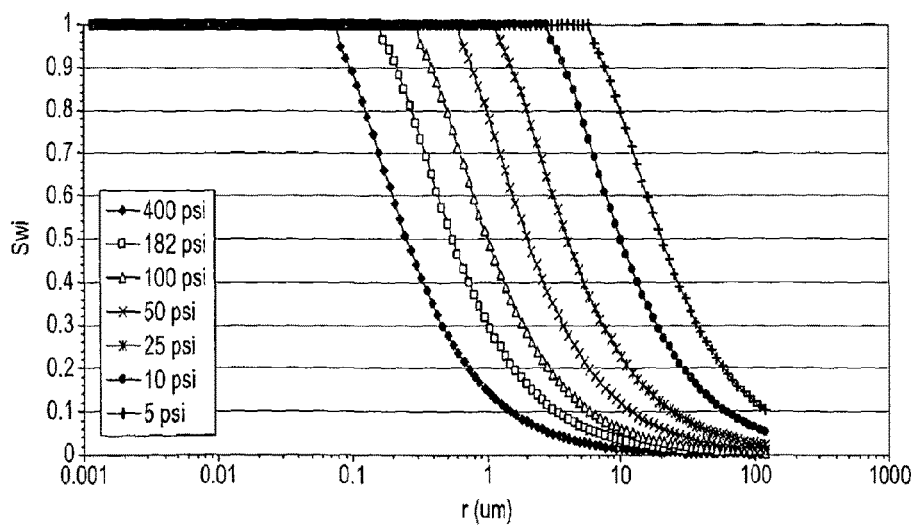
Figures 1, 2, 3:
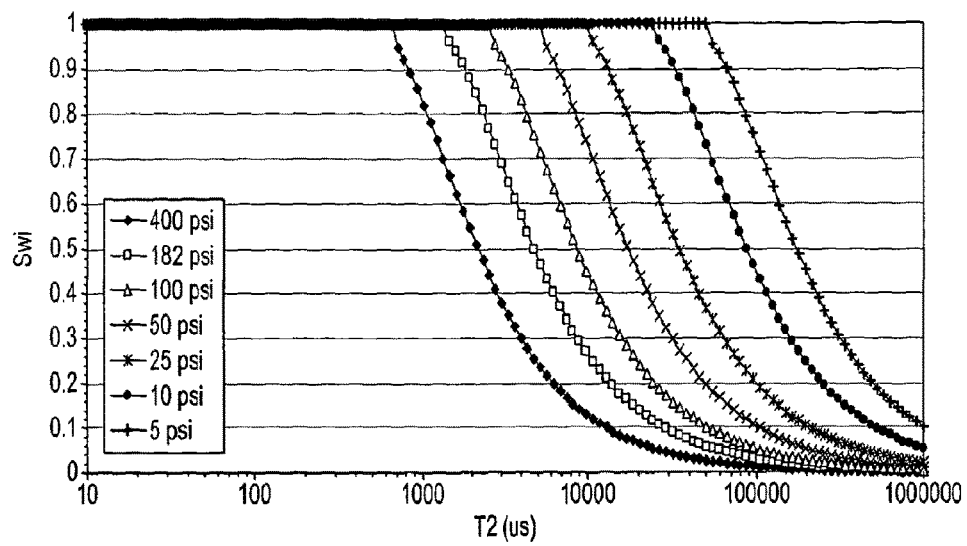

Accordingly, Equations (14a) and (15a) may be used to determine the initial water saturation as a function of pore size and, if desired, as a function of $T_2$ relaxation time, at a plurality of different capillary pressure (for example, at seven different capillary pressures), as shown in FIGS. 1-2 and 1-3, respectively.

Alternatively, the porous medium may be modelled as regular polygonal tubes when analyzing initial water saturation distribution at the pore scale and its relation to relaxation time $T_2$ distribution during the primary drainage process.

By applying Equation (2) to regular N-sided polygonal tubes (where N is an integer, for example, 3, 4, 5, or 6), we find that the $T_2$ relaxation time distribution of a fully water saturated regular polygonal tube is directly proportional to the apothem (L) of the regular polygons if we ignore the bulk relaxation and diffusion relaxation components of $T_2$:

$$T_{2,W1} = \frac{L}{2\rho_{2,w}} \quad (16)$$

Porous rocks are initially fully water saturated and strongly water wetted with a contact angle of zero. Where the porous medium is modelled as regular polygonal tubes, the capillary threshold pressure, $P_{Ct}$, is given by:

$$P_{Ct} = \frac{2\sigma}{L} \quad (17)$$

where L is the apothem of the regular N-sided polygon.

For the model that employs regular polygonal tubes, during a primary drainage process, a given tube can be invaded by non-wetting phase (e.g. oil or air) if the applied pressure just exceeds the threshold capillary pressure defined in Equation (17). Consequently, the non-wetting phase occupies the centre of the pore as a cylinder with radius of L.

As the applied pressure increases further, more and more water is displaced by the non-wetting phase. Consequently remaining water resides in the corners of the pore space and as a thin water film coating the pore walls. All the smaller pores whose threshold pressures are larger than the applied pressure cannot be invaded by the non-wetting phase and remain fully water saturated, e.g.:

$$S_{wi} = 1 \text{ for } P_c \leq P_{ct} \quad (18)$$

In pores of regular polygonal tubes that have been invaded by the non-wetting phase, the curvature radius ($R_c$) of the remaining water in the corners of the pore space is related to the capillary pressure ($P_c$) by $$R_c = \frac{2\sigma}{P_C} \quad (19)$$

For non-wetting phase invaded pores of regular N-sided polygonal tubes, the volume of the thin coating of the water film on the surface of pore walls can be ignored. Accordingly, the initial water saturation, $S_{wi}$, as a function of the $T_{2,W1}$ relaxation time, capillary pressure (Pc) and N can be determined using the following Equation:

$$S_{wi}(T_{2,W1}, P_C, N) = \left(\frac{\sigma}{P_C \rho_{2,w} T_{2,W1}}\right)^2 \left(1 - \frac{\pi}{N\tan(\pi/N)}\right) \quad (20a)$$

for $P_c > P_{ct}$, or $S_{wi} = 1$ for $P_c \le P_{ct}$

Similarly, the initial water saturation, $S_{wi}$, as a function of pore size (L), capillary pressure ($P_c$) and N can be determined using the following Equation:

$$S_{wi}(L, P_C, N) = \left(\frac{2\sigma}{P_C L}\right)^2 \left(1 - \frac{\pi}{N\tan(\pi/N)}\right) \quad (20b)$$

for $P_c > P_{ct}$, or $S_{wi} = 1$ for $P_c \le P_{ct}$ where, as discussed above, L is the apothem and N is the number of sides of the regular N-sided polygonal tubes.

For a two-phase system with water and oil, the initial oil saturation, $S_{Oi}$, as a function of the spin-spin relaxation time at 100% water saturation ($T_{2,W1}$), capillary pressure ($P_c$) and N can be determined by $$S_{Oi}(T_{2,W1}, P_C, N) = 1 - \left(\frac{\sigma}{P_C \rho_{2,w} T_{2,W1}}\right)^2 \left(1 - \frac{\pi}{N\tan(\pi/N)}\right) \quad (20c)$$

for $P_c > P_{ct}$, or $S_{Oi} = 0$ for $P_c \le P_{ct}$

Similarly, for a two-phase system with water and oil, the initial oil saturation, $S_{Oi}$, as a function of the pore size (L), capillary pressure ($P_c$) and N can be determined by $$S_{Oi}(L, P_C, N) = 1 - \left(\frac{2\sigma}{P_C L}\right)^2 \left(1 - \frac{\pi}{N\tan(\pi/N)}\right) \quad (20d)$$

for $P_c > P_{ct}$, or $S_{Oi} = 0$ for $P_c \le P_{ct}$

Substituting Equation (9) into Equations (12a), (12b), (13a), (13b), (20a), (20b), (20c), and (20d) gives initial fluid saturation distributions as a function of the height above free water level (H) in hydrocarbon bearing reservoirs.

The overall initial water saturation ($S_{wi}$) can be determined from the initial water saturation function ($S_{wi}(r, P_c)$) with respect to pore size (r), capillary pressure ($P_c$), and pore size distribution function $A_i(r)$ by $$S_{wi} = \sum_{i=1}^{n} S_{wi}(r, P_C) A_i(r) \quad (21)$$

It is observed that when modelling the porous medium with regular polygonal tubes, r can be replaced by L in equation 21.

Similarly, the overall initial water saturation ($S_{wi}$) can be determined by initial water saturation function ($S_{wi}(r, P_c)$) with respect to spin-spin relaxation time ($T_2$), capillary pressure ($P_c$), and spin-spin relaxation time ($T_2$) distribution function $A_i(T_2)$ by $$S_{wi} = \sum_{i=1}^{n} S_{wi}(T_2, P_C) A_i(T_2) \quad (22)$$

In a similar manner to Equation (1), for a 100% oil-saturated porous medium, the inverse of the spin-spin relaxation time ($T_2$) of the oil phase in a pore in the fast-diffusion limit may be expressed as:

$$\frac{1}{T_{2,O1}} = \rho_{2,O} \frac{A}{V} + \frac{1}{T_{2B,O}} \quad (23)$$

In Equation (23), $T_{2,O1}$ is the spin-spin relaxation time of fully oil saturated rock, $\rho_{2,O}$ is the spin-spin relaxivity of the oil phase, $T_{2B,O}$ is the bulk spin-spin relaxation time of the oil phase, A is the surface area of the pores within the porous medium and V is the pore volume.

For 100% oil-saturated large pores in a porous medium, the inverse of the spin-spin relaxation time ($T_{2,O1,L}$) of the oil phase in the large pores in the fast-diffusion limit may be expressed as:

$$\frac{1}{T_{2,O1,L}} = \rho_{2,O} \frac{A_L}{V_L} + \frac{1}{T_{2B,O}} \quad (24)$$

In Equation (24), $A_L$ is the surface area of the large pores within the porous medium and $V_L$ is the volume of the large pores.

The initial water and oil saturation models and their threshold capillary pressure ($P_{Ct}$), threshold pore-body radius ($r_t$) and threshold pore-throat radius ($R_t$), as well as threshold spin-spin relaxation time ($T_{2,t}$) developed in the present invention can be used to partition the pore size distribution into small pores with initial water saturation of 100% and larger pores that are initially saturated with water and oil. The cut-off pore radius ($r_c$) for the small pores will be dependent upon a number of factors including the capillary pressure, interfacial tension and pore geometry. The person skilled in the art would be able to select the cut-off pore radius for a particular hydrocarbon-bearing formation between the small pores that are 100% saturated with water and the larger pores initially saturated with both water and oil.

After primary drainage, oil invades the large pores in the reservoir. If the invaded oil phase does not contact the surface of the pore walls, the reservoir rocks remain water-wet and the oil phase only provides the bulk relaxation contribution to the relaxation time. If the oil phase starts to contact the surface of the pore walls, the contributions from both the surface relaxation mechanism and the bulk relaxation mechanism take effect, and the wettability alteration process occurs. After wettability alteration of a partially oil-saturated porous medium, the inverse of the spin-spin relaxation time ($T_2$) of the oil phase in a large pore in the fast-diffusion limit may be expressed as:

$$\frac{1}{T_{2,o,L}(S_{Oi})} = \rho_{2,Oi} \frac{A_{oiL}}{V_L S_{oiL}} + \frac{1}{T_{2B,O}} \quad (25)$$

In Equation (25), $T_{2,O,L}(S_{Oi})$ is the spin-spin relaxation time of the oil phase at initial oil saturation of $S_{Oi}$ of a partially oil saturated large pore, $S_{OiL}$ represents initial oil phase saturation of the oil invaded large pore, $\rho_{2,Oi}$ is the spin-spin relaxivity of the oil phase at initial oil phase saturation of $S_{Oi}$, $A_{oiL}$ is the surface area of the large pore contacted by oil phase, and $V_L$ is the volume of the large pore.

As wettability alteration during ageing, water flooding or EOR processes mainly occurs in oil bearing large pores, wettability indices for large pores can also be formulated. At initial oil saturation (Soi) condition, the oil phase wettability index for oil phase invaded large pores is defined as:

$$WI_{Oi,L} \frac{\rho_{2,oi} A_{oi,L}}{\rho_{2,o} A_L} = \frac{\left[\frac{1}{T_{2,o,L}(S_{oi})} - \frac{1}{T_{2B,O}}\right] S_{Oi,L}}{\frac{1}{T_{2,O1,L}} - \frac{1}{T_{2B,O}}} \quad (26a)$$

where $S_{oi,L}$ is initial oil saturation in the oil phase invaded large pores.

The present invention allows NMR wettability indices to be defined based on two factors, i.e., the fraction of the pore surface in direct contact with the fluid, and the relative surface relaxivity which is ratio of surface relaxivities at different saturation states for a porous medium (for the same porous medium). This newly defined relative surface relaxivity eliminates the influence of other factors on the surface relaxivity, for example, rock mineralogy and paramagnetic impurities that are present on the pore surface, and is directly related to the affinity between the pore surface and the fluids that are present in the pore space.

Similarly, at residual oil saturation ($S_{or}$) condition after water imbibition, water flooding, and/or an EOR process, oil phase wettability index ($WI_{or,L}$) for oil phase invaded large pores during a primary drainage process is defined as:

$$WI_{Or,L} = \frac{\left[\frac{1}{T_{2,o,L}(S_{Or})} - \frac{1}{T_{2B,O}}\right] S_{Or,L}}{\frac{1}{T_{2,O1,L}} - \frac{1}{T_{2B,O}}} \quad (26b)$$

where $S_{or,L}$ is residual oil saturation in the oil phase invaded large pores during a primary drainage process.

At residual oil saturation ($S_{or}$) condition after water imbibition, water flooding, and/or an EOR process, water phase wettability index ($WI_{W,L}$) for oil phase invaded large pores is defined as:

$$WI_{W,L} = \frac{\left[\frac{1}{T_{2,w,L}(S_{Or})} - \frac{1}{T_{2B,W}}\right] S_{W,L}}{\frac{1}{T_{2,W1,L}} - \frac{1}{T_{2B,W}}} \quad (26c)$$

where $S_{W,L}$ is water saturation at residual oil saturation in the oil phase invaded large pores during the primary drainage process.

By analyzing relaxation time ($T_2$) distributions at initial water and initial oil saturation state before and after core ageing, a spin-spin relaxation time cut-off ($T_{2,C}$) can be determined to further partition the pore volume of oil phase invaded large pores into smaller pores where wettability alteration does not occur and larger pores where wettability alteration does occur. Accordingly, the oil phase wettability index for those larger pores where wettability alteration occurs is defined as:

$$WI_{Oi,M} = \frac{\left[\frac{1}{T_{2,O,M}(S_{Oi})} - \frac{1}{T_{2B,O}}\right] S_{Oi,M}}{\frac{1}{T_{2,O1,M}} - \frac{1}{T_{2B,O}}} \quad (26d)$$

All the terms in equation (26d) are used to describe the wettability index, spin-spin relaxation time ($T_2$), and initial oil saturation in the larger pores where wettability alteration occurs after core ageing. $T_{2,O,M}(S_{Oi})$ is the spin-spin relaxation time of oil phase at initial oil saturation, $T_{2,O1,M}$ is the spin-spin relaxation time of oil phase at 100% oil saturation, and $S_{oi,M}$ is initial oil saturation in the oil phase invaded large pores where wettability alteration occurs after core ageing.

At initial oil saturation ($S_{oi}$) conditions, the wettability index for the oil phase as a function of both pore radius (r) and capillary pressure ($P_C$) is defined as:

$$WI_{Oi}(r, P_C) = \frac{\left[\frac{1}{T_{2,o}(S_{oi}, r, P_C)} - \frac{1}{T_{2B,O}}\right] S_{Oi}(r, P_C)}{\frac{1}{T_{2,O1}(r)} - \frac{1}{T_{2B,O}}} \quad (27)$$

It is observed that when modelling the porous medium with regular polygonal tubes, r can be replaced by L in equation 27.

Substituting Equation (12b) into Equation (27) gives wettability index (WI) of the oil phase as a function of pore size (r) and capillary pressure ($P_c$) for the pore-body and pore-throat model:

$$WI_{Oi}(r, P_C) = \frac{\left[\frac{1}{T_{2,O}(S_{oi}, r, P_C)} - \frac{1}{T_{2B,O}}\right]}{\frac{1}{T_{2,O1}(r)} - \frac{1}{T_{2B,O}}} \left(\frac{r - 2\sigma/P_C}{r}\right)^k \quad (28a)$$

if $r > r_t$; or $WI_{Oi} = 0$ if $r \leq r_t$

Substituting Equation (13b) into Equation (27) gives wettability index (WI) of the oil phase as a function of spin-spin relaxation time ($T_2$) and capillary pressure (Pc) for the pore-body and pore-throat model:

$$WI_{Oi}(T_2, P_C) = \frac{\left[\frac{1}{T_{2,O}(S_{oi}, r, P_C)} - \frac{1}{T_{2B,O}}\right]}{\left[\frac{1}{T_{2,O1}(r)} - \frac{1}{T_{2B,O}}\right]} \left(\frac{T_{2,W1} - \frac{2\sigma}{k\rho_{2,w} P_C}}{T_{2,W1}}\right) \quad (28b)$$

if $T_{2,W1} > T_{2t}$; or $WI_{Oi} = 0$ if $T_{2,W1} \leq T_{2t}$

Substituting Equation (20c) into Equation (27) gives wettability index (WI) of the oil phase as a function of spin-spin relaxation time ($T_2$) and capillary pressure ($P_c$) for the regular N-sided polygonal tubes model:

$$WI_{Oi}(T_2, P_C) = \frac{\left[\frac{1}{T_{2,O}(S_{oi}, r, P_C)} - \frac{1}{T_{2B,O}}\right]}{\left[\frac{1}{T_{2,O1}(r)} - \frac{1}{T_{2B,O}}\right]} \quad (29a)$$

$$\left[1-\left(\frac{\sigma}{P_C \rho_{2,w} T_{2,W1}}\right)^2\left(1-\frac{\pi}{N\tan(\pi/N)}\right)\right] \text{ if}$$

$T_{2,W1} > T_{2t}$; or $WI_{Oi} = 0$ if $T_{2,W1} \leq T_{2t}$

Substituting Equation (20d) into Equation (27) gives wettability index (WI) of the oil phase as a function of pore size (L) and capillary pressure ($P_c$) for the regular N-sided polygonal tubes model:

$$WI_{Oi}(L, P_C) = \frac{\left[\frac{1}{T_{2,O}(S_{oi}, r, P_C)} - \frac{1}{T_{2B,O}}\right]}{\left[\frac{1}{T_{2,Oi}(r)} - \frac{1}{T_{2B,O}}\right]}\left[1-\left(\frac{2\sigma}{P_C L}\right)^2\left(1-\frac{\pi}{N\tan(\pi/N)}\right)\right] \text{ for} \quad (29b)$$

$P_c > P_{ct}$, or $WI_{Oi} = 0$ for $P_c \leq P_{ct}$

Substituting Equation (9) into Equations (27), (28a), (28b), (29a), (29b) gives wettability indexes as a function of the height above free water level (H) in hydrocarbon bearing reservoirs.

It is noted that the relaxivity is influenced by surface affinity and the presence of any paramagnetic materials on or near the pore surface. The person skilled in the art will be aware that values for the relaxivity of fluids can be obtained from the literature, though these values may not always be reliably accurate. Additionally or alternatively, relaxivity values can be determined by experiment.

Let us consider a situation in which two fluid-saturated porous samples are taken or prepared, which samples contain a certain proportion of oil and water within their pores. Oil may be produced from one of the samples using a water flood or brine imbibition process, i.e. a secondary oil recovery process and from the other sample using a microbial or chemical EOR process, i.e. a tertiary oil recovery process.

In the former case (e.g. water flood), the inverse of the spin-spin relaxation time ($T_2$) of the water phase may be expressed as:

$$\frac{1}{T_{2,W}(Sor1)} = \rho_{2,W1}\frac{A_{W1}}{VS_{W1}} + \frac{1}{T_{2B,W1}} \quad (30)$$

In Equation (30), $T_{2,W}(S_{or1})$ is the spin-spin relaxation time of the water phase at residual oil saturation, $S_{or1}$, after the waterflood, $\rho_{2,wt}$ is the spin-spin relaxivity of the water phase after the waterflood, $T_{2B,W1}$ is the bulk spin-spin relaxation time of the water phase, $A_{W1}$ is the internal surface area of the pores that is in contact with the water phase after the waterflood, $S_{W1}$ is the water saturation level after the waterflood and V is the pore volume. In a two-phase system, it will be noted that $S_{w1}=(1-S_{or1})$.

In the latter case (e.g. after microbial EOR, hereinafter referred to as MEOR or after a chemical EOR process or after a low salinity water injection EOR process) the inverse of the spin-spin relaxation time ($T_2$) of the water phase may be expressed as:

$$\frac{1}{T_{2,W}(Sor2)} = \rho_{2,W2}\frac{A_{W2}}{VS_{W2}} + \frac{1}{T_{2B,W2}} \quad (31)$$

In Equation (31), $T_{2,W}(S_{or2})$ is the spin-spin relaxation time of the water phase at a second residual oil saturation, $S_{or2}$, after the EOR flood, $\rho_{2,w2}$ is the spin-spin relaxivity of the water phase after the EOR flood, $T_{2B,W2}$ is the bulk spin-spin relaxation time of the water phase, $A_{W2}$ is the internal surface area of the pores that is in contact with the water phase after the EOR flood, $S_{W2}$ is the initial water saturation level and V is the pore volume. In a two-phase system, it will be noted that $S_{w2}=(1-S_{or2})$.

Equations (30) and (31) can be normalized by reference to the situation for 100% water saturation (i.e. as described by equation (1) above), to give wettability indices according to the following equations:

$$WI_W = \frac{\rho_{2,W1}A_{W1}}{\rho_{2,w}A} = \frac{\left[\frac{1}{T_{2,w}(Sor1)} - \frac{1}{T_{2B,W1}}\right]S_{W1}}{\frac{1}{T_{2,W1}} - \frac{1}{T_{2B,W}}} \quad (32)$$

where Equation (32) gives the wettability index for the water phase after water flood or imbibition:

$$WI_{W,EOR} = \frac{\rho_{2,W2}A_{W2}}{\rho_{2,w}A} = \frac{\left[\frac{1}{T_{2,w}(Sor2)} - \frac{1}{T_{2B,W2}}\right]S_{W2}}{\frac{1}{T_{2,W1}} - \frac{1}{T_{2B,W}}} \quad (33)$$

where Equation (33) provides the wettability index for the water phase after an MEOR or EOR flood.

In spin-spin relaxation time distribution measurements of fluids within porous media, information regarding the distribution of the fluid within the pores and/or the structure of the pores may often be superimposed on one another. Hence, the above-described normalization is carried out, in order to decouple this superimposed information.

By dividing Equation (33) by Equation (32), an NMR wettability index modification factor ($WIMF_W$) may be derived for the water phase which compares, for example, EOR with a water flood process. This is shown in Equation (34) below:

$$WIMF_W = \frac{\rho_{2,W2}A_{W2}}{\rho_{2,W1}A_{W1}} = \frac{\left[\frac{1}{T_{2,w}(Sor2)} - \frac{1}{T_{2B,W2}}\right]S_{W2}}{\left[\frac{1}{T_{2,w}(Sor1)} - \frac{1}{T_{2B,W1}}\right]S_{W1}} \quad (34)$$

It should be noted that the definitions provided by Equations (33) and (34) are suitable for secondary or tertiary mode oil recovery processes.

Similarly, wettability indexes for oil phase after water flood (or imbibition) with residual oil saturation of Sor1 and EOR processes with residual oil saturation of Sor2 can be defined as equations (35) and (36), respectively:

$$WI_O = \frac{\rho_{2,O1}A_{O1}}{\rho_{2,O}A} = \frac{\left[\frac{1}{T_{2,O}(Sor1)} - \frac{1}{T_{2B,O}}\right]S_{Or1}}{\frac{1}{T_{2,O1}} - \frac{1}{T_{2B,O}}} \quad (35)$$

$$WI_{O,EOR} = \frac{\rho_{2,O2}A_{O2}}{\rho_{2,O}A} = \frac{\left[\frac{1}{T_{2,O}(S_{or2})} - \frac{1}{T_{2B,O}}\right]S_{Or2}}{\frac{1}{T_{2,O1}} - \frac{1}{T_{2B,O}}} \quad (36)$$

In equation (35), $WI_O$ is the wettability index for the oil phase after a water flood (or imbibition), $S_{or1}$ denotes a first residual oil saturation after the waterflood, $T_{2,o}(S_{or1})$ is the spin-spin relaxation time of the oil phase at the first residual oil saturation, $\rho_{2,o1}$ is the spin-spin relaxivity of the oil phase at the first residual oil saturation, $T_{2B,O}$ is the bulk spin-spin relaxation time of the oil phase, $A_{O1}$ is the internal surface area of the pores that is in contact with oil phase, $T_{2,O1}$ is the spin-spin relaxation time of oil phase for a porous medium that is fully saturated with the oil phase (100% oil phase saturation), $\rho_{2,O}$ is the spin-spin relaxivity of the oil phase, $T_{2B,O}$ is the bulk spin-spin relaxation time of the oil phase, and A is the surface area of the pores within the porous medium. Thus, equation (35) relates to a secondary oil recovery process.

In equation (36), $WI_{O,EOR}$ is the wettability index for the oil phase after an enhanced oil recovery flood, $S_{Or2}$ is the second residual oil saturation after the EOR flood, $T_{2,o}(S_{or2})$ is the spin-spin relaxation time of the oil phase at the second residual oil saturation, $\rho_{2,O2}$ is the spin-spin relaxivity of the oil phase at the second residual oil saturation, $T_{2B,O}$ is the bulk spin-spin relaxation time of the oil phase, $A_{O2}$ is the surface area of the pores within the porous medium in contact with oil phase, $T_{2,O1}$ is the spin-spin relaxation time of oil phase at 100% oil phase saturation, $\rho_{2,O}$ is the spin-spin relaxivity of the oil phase, $T_{2B,O}$ is the bulk spin-spin relaxation time of the oil phase and A is the total surface area of the pores within the porous medium. Thus, Equation 36 relates to a tertiary recovery process.

NMR Wettability Index Modification Factor ($WIMF_O$) for the oil phase when comparing an EOR process with a water flood (or imbibition) process is defined as:

$$WIMF_O = \frac{\left[\frac{1}{T_{2,O}(Sor2)} - \frac{1}{T_{2B,O}}\right]S_{Or2}}{\left[\frac{1}{T_{2,O}(Sor1)} - \frac{1}{T_{2B,O}}\right]S_{Or1}} \quad (37)$$

While the NMR wettability indices and wettability modification factors of equations (32) to (37) above have been defined in terms of the spin-spin relaxation time ($T_2$), it should be noted that they are also applicable to measurements of the spin-lattice relaxation time ($T_1$). When using $T_1$ instead of $T_2$, $\rho_1$ must be used instead of $\rho_2$ in the equations.

Also, it should be noted that NMR measurements of relaxation times generally record a relaxation time distribution. As will be described later, it is the peak values (i.e. most common relaxation time) or mean values from the appropriate distributions which are entered into the equations set out above.

A system for determining wettability characteristics of a fluid-bearing porous medium will now be described. The system includes data receiving means arranged to receive measurement data indicative of a relaxation time of fluid present in the porous medium at a defined fluid saturation. It should be understood that, as explained above, the fluid for which the relaxation time is measured may comprise an aqueous phase or an oil phase of fluid present in the porous medium. The defined fluid saturation may be, for example, initial oil saturation, residual oil saturation or water saturation at residual oil saturation, as defined with respect to equations (26a) to (26c) respectively.

The system further includes data receiving means arranged to receive reference data indicative of one or more reference relaxation times of the fluid; for example, the reference relaxation times in equation (26a) are the spin-spin relaxation time of the 100% oil saturated porous medium, and the bulk spin-spin relaxation time of the oil phase. Computer-implemented means, in the form of one or more software components such as a wettability index calculation component, are arranged to calculate the relevant wettability index (which, as described above, is indicative of the wettability characteristics of the porous medium). The wettability index is calculated on the basis of differences between the received measurement data and the received reference data, for example according to equations (26a) to (29b) and (32) to (36) defined above. The wettability index calculated is indicative of the wettability characteristics of the porous medium at the defined fluid saturation.

The system may also receive any other relevant data, such as data indicative of pore size, capillary pressure and/or residual oil saturation, required to calculate the wettability index.

The system can also comprise data receiving means arranged to receive a plurality of data, each of which is indicative of a relaxation time of fluid present in the porous medium. For example, the relaxation times may be measured at different points in time, at different locations in the porous medium, or at different stages before, after and/or during at least one of a primary, secondary or tertiary fluid recovery process, as will be described further below by reference to various Examples. In this case, the system comprises computer-implemented means, such as the wettability index calculation component, arranged to calculate the wettability index for each of the plurality of measurement data, respectively. The system further includes computer-implemented means arranged to calculate, on the basis of a comparison of the calculated wettability indices, the wettability index modification factor described above in equation (37). This latter calculation may be performed by a wettability index modification factor calculation component. The calculated wettability index modification factor is indicative of a change in the wettability characteristics of the porous medium.

The system is preferably a processing system comprising conventional operating system and storage components such as a system bus connecting a random access memory (RAM), a hard disk, a central processing unit (CPU), input/output adaptors facilitating connection to user input/output devices and, in some embodiments, interconnection with other devices on a network. The RAM contains operating system software which controls, in a known manner, low-level operation of the processing system. The RAM contains the wettability index calculation component, the wettability index modification factor calculation component, and any other software components, during execution thereof Each software component is configurable with measurement and/or predetermined data stored in one or more databases or other storage components which are operatively coupled or connected to the processing system.

The present invention will now be described by reference to the following Figures and Examples.

EXAMPLES

General Laboratory Procedures

Experiments demonstrating the principles of the present invention were carried out in the laboratory.

Experiments may be carried out on laboratory-prepared samples designed to simulate reservoir rock, e.g. sandpacks, or core plug samples taken from the field.

When using core plug samples, it may be preferred to take a single core plug and then to divide this up into a plurality of shorter so-called "sister plugs". This will help to ensure that the plug samples used in a particular experiment are as similar as possible.

In general, the samples or core plugs must first be prepared and aged.

For instance, where the sample is a core plug, it may initially contain many substances within its pores, e.g. connate water, drilling mud, crude oil. If deemed necessary, the core plug sample is cleaned using a solvent to remove these substances.

Once the sample has been cleaned (if necessary), it is then saturated with an aqueous phase, which phase may be intended to simulate the connate water which may be found within a particular reservoir.

An oil phase is then added to the sample, displacing a portion of the aqueous phase to provide a desired aqueous phase to oil phase ratio. In the laboratory, it may be possible to control conditions such that the sum of the initial oil phase saturation level ($S_{oi}$) and the initial aqueous phase saturation level ($S_{wi}$) equals unity, i.e. $S_{oi}+S_{wi}=1$. This means that the pores are completely full and only contain the two phases. In general, however, it is more probable that $S_{oi}+S_{wi}$ will be slightly less than unity, since other phases such as air may be present in small amounts within the pores.

The initial oil phase saturation level ($S_{oi}$) will be selected to replicate the conditions likely to be found within a reservoir. For instance, oil may be added to the sample in the required amount to give an initial oil saturation level of from 0.4 to 0.9. The initial oil saturation level may be, for example, about 0.4, 0.5, 0.6, 0.7, 0.8 or 0.9.

The sample is then allowed to age to allow the fluid, i.e. the aqueous phase and the oil phase to redistribute themselves within the pores of the sample until an equilibrium distribution is reached.

For instance, it will be appreciated that when the sample is saturated with aqueous phase (i.e. before any oil is added), the aqueous phase will occupy the entire pore volume of the sample. Considering a single pore, when oil is added to the sample, initially the oil phase will generally displace aqueous phase from the bulk region of the pore. Aqueous phase will remain in contact with the pore surfaces. During ageing the oil phase and aqueous phase will redistribute within the pore, e.g. such that a portion of the pore surface is contacted by oil phase. Accordingly, after aging, the pore will be in a mixed wettability state.

Wettability controls the fluid distribution in a reservoir and therefore exerts a fundamental influence on flow behaviours, residual oil saturation and relative permeability. Accordingly, wettability also has a fundamental influence on reservoir performance. Therefore, it is most desirable that the wettability distribution within a test sample is representative of the reservoir.

Accordingly, it is important that the ageing process is allowed to run its course before a sample is used in any subsequent experiments. If ageing is not complete or is not substantially complete, then any predictions based on the results of such subsequent experiments may be prone to a higher degree of error, since the sample will not closely replicate reservoir conditions.

Complete or sufficient ageing of a sample may take a long time, for instance sometimes of the order of several weeks or even months.

By taking regular $T_2$ distribution measurements, the ageing process may be monitored. For example, $T_2$ distribution measurements may be taken every day or every few days.

The $T_2$ distribution will change as the phases redistribute between the pores, e.g. as more oil contacts the pore surfaces. When the sample has aged sufficiently or completely, the $T_2$ distribution will no longer change significantly from taking one measurement to the next. Conveniently, the ageing process can be tracked by observing and plotting the trend in the logarithmic mean of the $T_2$ distribution, which will tend to settle at or around a particular value towards the end of the ageing process.

Where test samples are obtained from core samples, reservoir wettability may be restored by cleaning the or each core sample with a solvent, followed by acquisition of representative initial oil and water saturation, and ageing (e.g. by soaking) in crude oil for a period of time to re-establish reservoir wettability.

Imbibition (oil displacement) experiments may be carried out on the test samples. These may be forced imbibition experiments or spontaneous imbibition experiments.

The various $T_2$ relaxation time measurements may be taken using a Carr-Purcell-Meiboom-Gill (CPMG) pulse sequence with an echo time of 0.2 ms, and a resonance frequency of 2 MHz. The obtained CPMG data may be inverted to a $T_2$ relaxation time distribution using an inverse Laplace transformation algorithm.

Example 1

NMR Wettability Studies During Core Ageing and Low Salinity Water and High Salinity Seawater Imbibition Processes Two sandstone reservoir core plug samples #156 and #157 were selected as a pair. The plugs were cleaned using a flow through method with hot solvents.

After core cleaning the plugs were characterized. The diameters of the plug samples #156, and #157 were 3.8 cm and their lengths were 7.7 cm and 7.6 cm, respectively. The core plug samples #156 and #157 had a porosity of approximately 0.15 and a permeability of approximately 25 mD.

The two core plug samples were driven to initial water saturation ($S_{wi}$) of 0.2 by nitrogen gas using the confined porous plate technique with capillary pressure of 182 psi.

The two core samples were inserted into hydrostatic core-holders and a nominal overburden pressure of 400 psi was applied. The two core plugs were saturated with kerosene at initial water saturation (Swi) condition. Crude oil samples were heated to the reservoir temperature of 68° C. and were injected into the core samples via a 0.5 micron filter. Prior to the injection of the crude oil, the kerosene was displaced by a buffer of toluene to prevent deposition of asphaltenes from the crude oil which can otherwise occur if crude oil contacts kerosene. The two core plug samples at initial water saturation ($S_{wi}$) and initial oil saturation ($S_{oi}$) were heated to a temperature of 68° C. in the hydrostatic core holders and were then aged for a period of three weeks. A 1.5 pore volume of crude oil was refreshed weekly during the ageing period.

The two core plugs underwent investigation of NMR relaxation time $T_2$ distributions at each stage of their saturation history:

- at 100% water Saturation;
- at initial water saturation ($S_{wi}$) and initial oil saturation ($S_{oi}$) prior to core ageing;
- at initial water saturation ($S_{wi}$) and initial oil saturation ($S_{oi}$) post core ageing;
- at residual oil saturation ($S_{or}$) post imbition (with seawater or low salinity brine)
- at 100% oil saturation.

In addition, the NMR relaxation time $T_2$ response was measured on a bulk sample of the crude oil and on bulk water samples (seawater and low salinity brine).

A synthetic formation brine composition was used as the aqueous phase within the aged plug samples. Details of the composition of the synthetic brine are given below in Table 1-1.

TABLE 1-1

| Component | Concentration (g/l) |
|---|---|
| $NaHCO_3$ | 1.315 |
| $Na_2SO_4$ | 0.037 |
| $Na_2CO_3$ | 0.000 |
| $CaCl_2 2H_2O$ | 1.367 |
| $MgCl_2 6H_2O$ | 0.217 |
| $FeCl_3$ | 0.000 |
| $BaCl_2 2H_2O$ | 0.009 |
| KCl | 0.200 |
| $SrCl_2 6H_2O$ | 0.067 |
| LiCl | 0.011 |
| NaCl | 11.359 |

Following core aging, the two core plugs were placed in imbibiometers. Core plug #156 was submerged in a low salinity brine and core plug #157 was submerged in synthetic seawater. The imbibiometers were placed inside a laboratory oven and were maintained at a temperature of 68° C. The oil produced due to spontaneous imbibition was monitored.

The composition of the synthetic seawater is set out below in Table 1-2.

TABLE 1-2

| Component | Component Concentration (g/l) |
|---|---|
| $NaHCO_3$ | 0.19 |
| $Na_2SO_4$ | 3.92 |
| $CaCl_2 2H_2O$ | 1.47 |
| $MgCl_2 6H_2O$ | 10.64 |
| KCl | 0.72 |
| NaCl | 23.48 |

The low salinity brine was obtained by diluting the synthetic seawater with de-ionised water such that the total dissolved solids content was 1500 ppm by mass.

The two brine imbibition experiments showed that the water saturation level rose faster and reached a higher final value for the low salinity brine (core plug sample #156) than for the high salinity brine (core plug sample #157). The eventual difference in water saturation after 42 days imbibition was 4.2 saturation units (42.2% for high salinity brine and 46.4% for low salinity brine (see Table 1-3)).

Table 1-3 Results of Spontaneous Imbibition experiments for plug samples #156 and #157

TABLE 1-3

| Plug number | $S_{oi}$ | $S_{or}$ | Oil Production (fraction OOIP) |
|---|---|---|---|
| 156 | 0.79 | 0.54 | 0.32 |
| 157 | 0.80 | 0.58 | 0.27 |

FIG. 1-1 shows the $T_2$ relaxation time distributions for sister rock core plugs # 156 and #157 at 100% water saturation ($S_w=1$). The relaxation time distributions for the two plugs at 100% water saturation were almost identical indicating that the two plugs have very similar pore size distributions.

A porous plate experiment was carried out for the two rock core plugs, #156 and #157, with air displacing water, where $\theta=0$, and $\sigma=72$ mN/m. The applied capillary pressure was 182 psi (i.e., Pc=182 psi (1.25 MN/m$^2$)), which corresponded to a threshold capillary pore throat radius ($R_t$) of 0.11 μm, determined using Equation (8). The measured overall initial water saturation was 0.2.

The initial water saturation ($S_{wi}$) distribution as a function of pore size for a cylindrical pore throat and spherical pore body model (Equation 14a) was used to match the determined overall initial water saturation of 0.2 at capillary pressure of 182 psi with Equation (21) thereby providing matching parameters of effective water relaxivity, $\rho_{2,w}$, of 26.1 μm/s, and a pore body-to-throat ratio (BTR) of 1.5. The determined matching parameters were employed in Equation (14a) to determine initial water saturation distribution as a function of pore size at six different capillary pressures, i.e. 5, 10, 25, 50, 100 and 400 psi, as shown in FIG. 1-2.

Similarly, the initial water saturation ($S_{wi}$) distribution as a function of relaxation time ($T_2$) for a cylindrical pore throat and spherical body model (Equation 15a) was used to match the determined overall initial water saturation of 0.2 at capillary pressure of 182 psi with Equation (22) thereby providing matching parameters of effective water phase relaxivity, $\rho_{2,w}$, of 26.1 μm/s and BTR of 1.5. The determined matching parameters were employed in Equation (15a) to determine initial water saturation distribution as a function of relaxation time ($T_2$) at six different capillary pressures, i.e. 5, 10, 25, 50, 100 and 400 psi, as shown in FIG. 1-3.

Water volume distributions as a function of pore size (r) at 100% water saturation (Sw=1) and at initial water saturation ($S_{wi}=0.2$) were determined for core plug #156 at a capillary pressure of 182 psi; these are shown in FIG. 1-4. The water volume distributions were calculated from the cylindrical pore throat and spherical body model (Equation (14a)) with a BTR of 1.5, an effective water phase relaxivity, $\rho_{2,w}$, of 26.1 μm/s, and a surface tension of 72 mN/m. The water volume distribution as a function of pore size curve at fully water saturated condition ($S_w=1$) in FIG. 1-4 was converted from the relaxation time $T_2$ distribution curve of core plug #156 of FIG. 1-1. The initial water volume distribution as a function of pore size curve of FIG. 1-4 was determined by multiplying the amplitudes in the fully water-saturated curve of FIG. 1-4 by the corresponding initial water saturation value ($S_{wi}$) for the curve at a capillary pressure of 182 psi shown in FIG. 1-2.

The initial oil volume distribution as a function of pore size at a capillary pressure of 182 psi and at initial oil saturation of 0.2 for core plug #156 is shown in FIG. 1-5 and was calculated from the cylindrical pore-throat and spherical pore-body model (Equation (14b)) with a BTR of 1.5, effective water phase relaxivity, $\rho_{2,w}$, of 26.1 μm/s, and a surface tension of 72 mN/m.

The initial water volume distribution as a function of pore size at fully water saturated condition ($S_w$=1) and at initial water saturation ($S_{wi}$=0.2) for core plug #157 at a capillary pressure of 182 psi is shown in FIG. 1-6 These were calculated from the cylindrical pore-throat and spherical pore-body model (Equation (14a)) with a BTR of 1.5, an effective water phase relaxivity, $\rho_{2,w}$, of 26.1 μm/s, and a surface tension of 72 mN/m. The water volume distribution as a function of pore size at fully water saturated condition ($S_w$=1) of FIG. 1-6 was converted from the relaxation time $T_2$ distribution curve of core plug #157 (FIG. 1-1). The initial water volume distribution as a function of pore size curve in FIG. 1-6 was determined by multiplying the amplitudes of the fully water-saturated curve in FIG. 1-6 by the corresponding initial water saturation value ($S_{wi}$) (of the 182 psi curve in FIG. 1-2).

The initial oil volume distribution as a function of pore size at a capillary pressure of 182 psi and at initial oil saturation of 0.2 for core plug #157 is shown in FIG. 1-7 and was calculated from the cylindrical pore-throat and spherical pore-body model (Equation (14b)) with a BTR of 1.5, effective water phase relaxivity, $\rho_{2,w}$, of 26.1 μm/s, and a surface tension of 72 mN/m.

The initial oil saturation as a function of pore size at a capillary pressure of 182 psi and corresponding overall initial oil saturation of 0.8 for sister core plugs #156 and #157 is shown in FIG. 1-8. This was calculated from the cylindrical pore throat and spherical pore body model and Equation (14b) with a BTR of 1.5, effective water phase relaxivity, $\rho_{2,w}$, of 26.1 μm/s, and a surface tension of 72 mN/m.

FIG. 1-9 shows relaxation time ($T_2$) distributions for a bulk crude oil (labelled Bulk crude) and for core plug #156 at different saturation states i.e. at 100% brine saturation (labelled SW1), at 100% oil saturation (labelled So1), at initial oil and water saturation before ageing (labelled Swi) and after ageing for three weeks (labelled Aged@Swi), and after spontaneous imbibition with low salinity water (labelled as Imbibition).

Comparing the relaxation time $T_2$ distributions for core plug #156 before and after ageing for the large pores showed that $T_2$ relaxation time distribution of the aged rock sample was shorter than for the un-aged rock sample. This arises because the oil phase contacts the surface of the pore walls and results in wettability alteration in the large pores. In the large pores, ageing process shifts the $T_2$ relaxation time distribution to the left hand side, with similar scale, whist retaining a similar shape. Therefore, the ageing process in the large pores shifts the overall $T_2$ relaxation time distribution shift to shorter $T_2$ relaxation times. This can be approximately represented by a shift of peak values of the $T_2$ relaxation time from 41884 μs to 31910 μs. This shift is employed in Equation (28a) for calculating the oil phase wettability index distribution as a function of pore size after aging. The peak values of $T_2$ relaxation time for bulk crude oil and 100% oil saturated core plugs are also employed as inputs into the Equation (28a). The determined wettability index as a function of pore size is shown in FIG. 1-11 for core plug #156.

The results presented in FIG. 1-9 show that the $T_2$ relaxation time distributions at initial water and oil saturation before and after ageing were almost unchanged for $T_2$ relaxation time components less than 2521 μs, these components reflect $T_2$ relaxation time distributions of initial water and oil in small pores which remain strongly water-wet with a wettability index of the oil phase of zero after ageing. Applying a $T_2$ relaxation time cut-off ($T_{2C}$) of 2521 μs to the relaxation time $T_2$ distribution at initial water and oil saturation before ageing, the total initial water and oil saturation in the small pores was determined as 0.214 PV (pore volume). Before ageing, the initial oil phase did not contact the rock grain surface and remained as the non-wetting phase and therefore displayed bulk relaxation characteristics in the rock.

Applying a $T_2$ relaxation time cut-off of 2521 μs to the $T_2$ relaxation time distribution of bulk crude oil, the pore volume ratio of initial oil phase in the small pores to the total initial oil phase was determined to be 0.093, which gives the amount of initial water phase completely covering the surface of a pore wall as 0.14 PV. In addition, in the small pores, there is 0.074 PV of initial oil phase not in contact with the pore wall surface after ageing. Applying the determined initial oil saturation of 0.074 PV in the small pores to the oil phase volume distribution as a function of pore size, a cut-off value of pore radius, $r_c$, of 1 μm was determined. This gave a boundary condition achieving a contact angle (θ) of zero, as well as a wettability index of the oil phase (WIoi) of zero and a wettability index of the water phase (WIwi) of 1, for a pore radius less than 1 μm, i.e., θ=0, and WIoi=0, and WIwi=1 for r<$r_c$.

The peak values of $T_2$ relaxation time distributions of the oil phase for core plug sample #156 at initial oil saturation after aging ($T_{2,O}$(Soi)), at 100% oil phase saturation ($T_{2,O1}$) as well as the peak value of relaxation time ($T_2$) for a bulk crude oil sample ($T_{2B,O}$) are shown in Table 1-4 below:

TABLE 1-4

| $T_{2B,O}$ (ms) | $T_{2,O1}$ (ms) | $T_{2,O}$(SOi) (ms) |
|---|---|---|
| 50.21 | 26.619 | 31.91 |

Using the determined initial oil saturation in the large pores, i.e. $S_{Oi,M}$=0.912, and peak values of $T_2$ relaxation time distributions (shown in Table 1-4) as inputs into the wettability index calculation component, the wettability index calculation component executes steps according to Equation (26d), and outputs a value of 0.59 for the average wettability index for the oil phase in the larger pores after ageing ($WI_{oi,M}$=0.59).

FIG. 1-10 shows relaxation time ($T_2$) distributions for a bulk crude oil (labelled Bulk crude) and for core plug #157 at different saturation states i.e. at 100% brine saturation (labelled SW1), at 100% oil saturation (labelled So1), at initial oil and water saturation before ageing (labelled Swi) and after ageing for three weeks (labelled Aged), and after spontaneous imbibition with high salinity water (labelled as Imbibition).

Comparing the $T_2$ relaxation time distributions for core plug #157 before and after ageing for the large pores showed that the $T_2$ relaxation time distribution of the aged rock sample was shorter than for the un-aged rock sample. This arises because the oil phase contacts the surface of the pore walls and results in wettability alteration in the large pores. In the large pores, the ageing process shifts the $T_2$ relaxation time distribution to the left hand side, with a similar scale, whist retaining a similar shape. Therefore, the ageing process in the large pores shifts the overall $T_2$ relaxation time distribution to shorter $T_2$ relaxation times. This can be approximately represented by a shift of peak values of the $T_2$ relaxation time from 50210 μs to 38254 μs. This shift is employed in Equation (28a) for calculating the oil phase wettability index distribution as a function of pore size after aging. The peak values of the $T_2$ relaxation time for bulk crude oil and 100% oil saturated core plugs are also employed as inputs into the wettability index calculation component, which executes steps according to the Equation (28a). The determined wettability index as a function of pore size is then output by the wettability index calculation component and is shown in FIG. 1-12 for core plug #157.

The results presented in FIG. 1-10 show that the $T_2$ relaxation time distributions at initial water and oil saturation before and after ageing were almost unchanged for $T_2$ relaxation time components of less than 3309 μs; these components reflect $T_2$ relaxation time distributions of the initial water and oil in small pores which remain strongly water-wet with a wettability index of the oil phase of zero after ageing. Applying a $T_2$ relaxation time cut-off ($T_{2C}$) of 3309 μs to the $T_2$ relaxation time distribution at the initial water and oil saturation before ageing, the total initial water and oil saturation in the small pores was determined as 0.2524 PV (pore volume). Before ageing, the initial oil phase did not contact the rock grain surface and remained as the non-wetting phase and therefore displayed bulk relaxation characteristics in the rock.

Applying a $T_2$ relaxation time cut-off of 3309 μs to the $T_2$ relaxation time distribution of bulk crude oil, the pore volume ratio of initial oil phase in the small pores to the total initial oil phase was determined to be 0.1189, which gives the amount of initial water phase completely covering the surface of a pore wall as 0.1586 PV. In addition, in the small pores, there is 0.0938 PV of initial oil phase not in contact with the pore wall surface after ageing. Applying the determined initial oil saturation of 0.0938 PV in the small pores to the oil phase volume distribution as a function of pore size, a cut-off value of pore radius, $r_c$, of 1 μm was determined. This gave a boundary condition achieving a contact angle (θ) of zero, as well as a wettability index of the oil phase (WIoi) of zero and a wettability index of the water phase (WIwi) of 1, for a pore radius less than 1 μm, i.e., θ=0, and WIoi=0, and WIwi=1 for r<$r_c$.

The peak values of $T_2$ relaxation times of the oil phase for core plug sample #157 at initial oil saturation after aging ($T_{2,O}$(Soi)), at 100% oil phase saturation ($T_{2,O1}$) as well as the peak value of relaxation time ($T_2$) for a bulk crude oil sample ($T_{2B,O}$) are shown in Table 1-5 below:

TABLE 1-5

| $T_{2B,O}$ (ms) | $T_{2,O1}$ (ms) | $T_{2,O}$(Soi) (ms) |
|---|---|---|
| 50.21 | 29.145 | 38.254 |

Using the determined initial oil saturation in the large pores, i.e. $S_{oi,M}$=0.939, and peak values of $T_2$ relaxation time distributions (shown in Table 1-5) as inputs into the wettability index calculation component, the wettability index calculation component executes steps according to Equation (26d), and outputs a value of 0.41 for the average wettability index for the oil phase in the larger pores after ageing ($WI_{oi,M}$=0.41).

Table 1-6 shows the peak values of $T_2$ relaxation times of the oil phase for core plug sample #156 at residual oil saturation after spontaneous low salinity brine imbibition ($T_{2,O}$(Sor)) and at the 100% oil phase saturation ($T_{2,O1}$) as well as the peak value of $T_2$ relaxation time for a bulk crude oil sample ($T_{2B,O}$) and the value of residual oil saturation ($S_{or,L}$) in the oil phase invaded large pores after spontaneous low salinity brine imbibition.

TABLE 1-6

| $T_{2B,O}$ (ms) | $T_{2,O}$(So = 1) (ms) | $T_{2,O}$(Sor) (ms) | $S_{or,L}$ |
|---|---|---|---|
| 50.21 | 26.619 | 50.21 | 0.56 |

The NMR oil phase wettability index for core plug sample #156 at residual oil saturation (Sor) after spontaneous low salinity brine imbibition was determined by the wettability index calculation component using Equation (26b) and the data in Table 1-6, giving an output oil phase wettability index of 0, indicating a strongly water wet state. Table 1-7 shows the peak values of $T_2$ relaxation times of oil phase for core plug sample #157 at residual oil saturation after spontaneous high salinity seawater imbibition ($T_{2,O}$(Sor)) and at 100% oil phase saturation ($T_{2,O1}$) as well as the peak value of relaxation time ($T_2$) for a bulk crude oil sample ($T_{2B,O}$) and the value of residual oil saturation ($S_{or,L}$) in the oil phase invaded large pores after spontaneous high salinity seawater imbibition.

TABLE 1-7

| $T_{2B,O}$ (ms) | $T_{2,O1}$ (ms) | $T_{2,O}$(Sor) (ms) | $S_{or,L}$ |
|---|---|---|---|
| 50.21 | 29.145 | 41.884 | 0.60 |

The NMR oil phase wettability index for core plug sample #157 at residual oil saturation after spontaneous sea water imbibition can be calculated by the wettability index calculation component using equation (26b) and data in Table 1-7, which gives an output oil phase wettability index of 0.17, indicating a mixed wet state.

The NMR studies of the pair of core plugs #156 and #157 shows that low salinity brine spontaneous imbibition results in a more water wet state than sea water imbibition, and consequently increased oil recovery.

Example 2

NMR Wettability Studies for Waterflooding with High Salinity Brine and Different Low Salinity Brines In this example, waterflood experiments were carried out on three sister core plug samples using different salinity brines as injection water.

The permeability of the core plug samples was 158 mD. The samples were prepared and aged to an initial aqueous phase saturation of 17.6% (i.e. $S_{wi}$=0.176). The aqueous phase was a synthetic formation water. The oil phase was stock tank oil (STO).

The first of the three sister core plugs was subjected to a high salinity formation water flood. The total dissolved solids (TDS) content of the high salinity water was 33435 mg/l.

The second of the three sister core plugs was subjected to a low salinity brine #1 (secondary mode) water flood. The TDS content of the low salinity brine #1 was 3144 mg/l.

The third of the three sister core plugs was subjected to a low salinity brine #2 (secondary mode) water flood. The TDS content of the low salinity brine #2 was 441 mg/l.

FIG. 2-1 shows the $T_2$ relaxation time distributions for the following samples: (i) bulk STO; (ii) one of the core plugs at 100% water saturation (labelled SW1) (iii) one of the core plugs after ageing at initial water and initial oil saturation; (iv) the first of the three sister core plugs at residual oil saturation after high salinity water flood (labelled High salinity Sor); (v) the second of the three sister core plugs at residual oil saturation after low salinity brine #1 water flood (labelled as Low salinity #1 Sor; and (vi) the third of the three sister core plugs at residual oil saturation after low salinity brine #2 water flood (labelled Low salinity #2 Sor).

In FIG. 2-1, a mixed wetting state signature is identified from $T_2$ relaxation time distributions at residual oil saturation after the three different salinity water floods with, in each case, a higher $T_2$ peak relaxation time than those of bulk crude oil and fully water saturated core plug.

FIG. 2-1 clearly shows that the main components of the $T_2$ relaxation time distribution of the sample aged with STO at initial water saturation (Swi) of 17.6% has been shifted to the left hand side in comparison with the $T_2$ relaxation time distribution of the bulk STO. This may be because of surface relaxation effects when oil phase is in contact with pore surfaces after ageing owing to an alteration in the wetting state of the sample.

The three $T_2$ relaxation time distributions for the three sister core plugs after their respective water floods show significant shape changes from the $T_2$ relaxation time distribution of the aged sample with a significant reduction of the oil peaks and the emergence of additional peaks on the right hand side of the spectrum. The new additional components have relaxation time values larger than the longest relaxation time value for the bulk STO. These components, therefore, clearly result from the injection water and furthermore confirm the development of a mixed wetting state. Since significant parts of the pore surface have become covered by crude oil, the surface areas in contact with the injection water has been limited which results in a dramatic increase in the $T_2$ relaxation time for the injection water. The $T_2$ relaxation time for the injection water, however, is less than that of the bulk water owing to partial contact of the injection water with the pore surface. Further analysis of the $T_2$ distributions for the main components of the injection water clearly shows a decreasing trend of relaxation time with decreasing salinity of the injection water. This indicates wettability alteration, with a decreasing oil wet tendency as the salinity of the injection water is reduced. The lowest oil wet tendency is observed for the optimized low salinity water.

Using the definition of wettability index modification factor described previously, the change of wettability during different salinity oil recovery processes is analyzed quantitatively. FIG. 2-1 shows that all the components of the $T_2$ relaxation time of bulk STO are less than 160 ms. Therefore, after water flooding the components of the $T_2$ distribution longer than 160 ms must arise from the water phase. Thus, the logarithmic mean values of relaxation time distributions longer than 160 ms are calculated as $T_{2w}$(Sor1)=580 ms, $T_{2w}$(Sor2)=446 ms, $T_2$(Sor3)=393 ms, for high salinity water flood, low salinity water flood, and optimised low salinity water flood, respectively. The core flood determined residual oil saturations are $S_{or1}$ of 0.469, $S_{or2}$ of 0.321, and $S_{or3}$ of 0.224, which corresponds to $S_{W1}$ of 0.531, $S_{W2}$ of 0.679, and $S_{W3}$ of 0.776 for high salinity water flood, low salinity water flood, and optimized low salinity water flood, respectively. The bulk relaxation time for the water phase is $T_{2B,W}$=2298 ms. The $T_2$ relaxation time values determined at residual oil saturations after the high salinity water flood, after the low salinity water flood (low salinity brine #1), and after the optimized low salinity water flood, (low salinity brine #2) were inputted into Equation (34). By comparison with the high salinity water flood, the calculated water phase wettability index modification factors ($WIMF_w$) calculated and output by the wettability index modification factor calculation component using Equation (34) were 1.79 and 2.39 for low salinity water flood and optimised low salinity water flood, respectively.

The experimental results show that in comparison with a high salinity water flood, both the oil recovery factor and water phase wettability index have been significantly improved by the low salinity water flood and the optimised low salinity water flood.

Example 3

NMR Wettability Study for an MEOR Core Flood

In this example, three sister core plugs were employed having a porosity of approximately 30% and permeability of approximately 130 mD. NMR $T_2$ relaxation time distributions were obtained at 100% formation water saturation (SW1), at 100% crude oil saturation (So1), at residual oil saturation after MEOR core flooding at reservoir conditions, and subsequent to 47 days diffusion of the core plug in a deuterium oxide ($D_2O$) reservoir to obtain the relaxation time distribution of the oil phase only at residual oil saturation conditions after the MEOR process at reservoir conditions. The NMR $T_2$ relaxation time distributions were also obtained for a bulk crude oil sample.

A pore body and throat model was used. The initial water saturation as a function of $T_2$ relaxation time and as a function of pore size is shown in FIGS. 3-1 and 3-2 respectively for the MEOR core plugs at a capillary pressure of 100 psi (0.689 MN/m$^2$). The water volume distribution is shown in FIG. 3-3 as a function of pore-body radius at 100% water saturation (Sw=1) and at irreducible (initial) water saturation (Swi=0.28). The initial water saturation in oil non-invaded small pores (Swis) determined using the pore body and throat model is 0.097 which is consistent with the total water saturation of a small peak at the left hand side of the $T_2$ relaxation time distribution of a fully water saturated core plug.

Figures 1, 2, 3, 4:
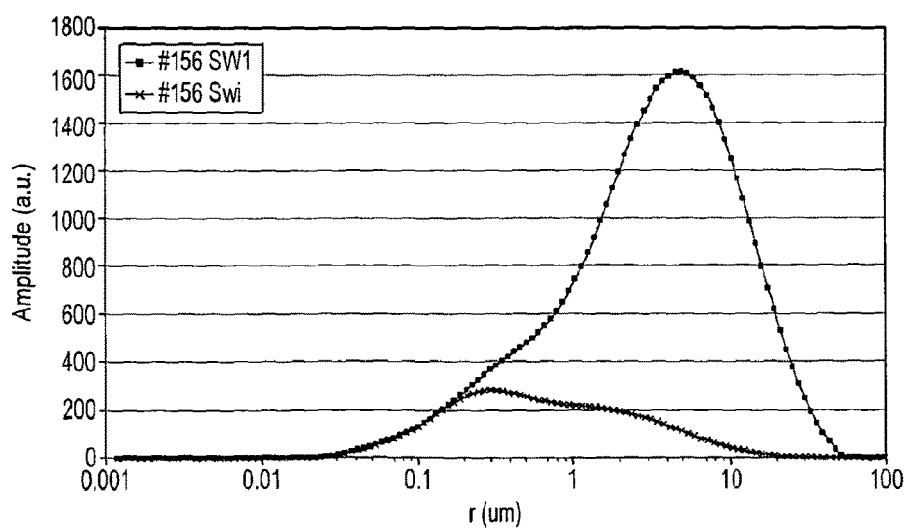

FIG. 3-4 shows the $T_2$ relaxation time distributions of bulk crude oil (labelled as crude), core plugs at 100% water saturation condition (labelled as SW1) and at 100% oil saturated condition (labelled as So1) as well as at residual oil saturation condition after an MEOR core flood at reservoir conditions (labelled as Sor+Swor) and after diffusion of the core plug for 47 days in a large deuterium oxide ($D_2O$) reservoir at the MEOR residual oil saturation (Sor) conditions (labelled as Sor D2O). The deuterium oxide ($D_2O$) replaced water ($H_2O$) that was originally present in the core plug allowing the $T_2$ relaxation time distribution of the oil phase (Sor) to be determined; this is because deuterium oxide ($D_2O$) cannot be detected with the low field NMR spectrometer. The $T_2$ relaxation time distribution of the water phase at the MEOR residual oil saturation (labelled Swor) was determined by subtraction of the residual oil phase signal (Sor D2O) from the $T_2$ relaxation time distribution after MEOR core flood at reservoir conditions (labelled as Sor+Swor).

Table 3-1 shows peak $T_2$ relaxation time values of the relaxation time distributions shown in FIG. 3-4 for bulk crude oil and core plugs at different saturation conditions before and after MEOR, as well as residual oil saturation ($S_{orL}$) and water saturation ($S_{wL}$) in oil invaded large pores during primary drainage process.

TABLE 3-1

| $T_{2B,O}$ (ms) | $T_{2,W}$ (Sw = 1) (ms) | $T_{2,O}$ (So = 1) (ms) | $T_{2W}$ (Sor) (ms) | $S_{wL}$ | $T_{2,O}$ (Sor) (ms) | $S_{orL}$ |
|---|---|---|---|---|---|---|
| 68.335 | 54.974 | 26.619 | 60.19 | 0.732 | 38.934 | 0.268 |

After MEOR, the wettability index (of oil invaded large pores during the primary drainage process) calculated and output by the wettability index calculation component is 0.13 for the oil phase ($WI_{or,L}$), and 0.67 for the water phase ($WI_{W,L}$). These values were calculated by the wettability index calculation component using Equations (26b) and (26c) respectively. This result shows that the MEOR core flood process at reservoir conditions results in the core plug samples having a more water-wet and less oil-wet state.

Example 4

Sandpack Experiments

In this example, spontaneous imbibition experiments were carried out on two sandpacks, #110, 210, that were intended to simulate a porous rock formation. The sandpacks were prepared by initially saturating a produced sand (obtained from an oil reservoir) in brine, and partially drying the sand to remove excess brine. The sand/brine was then mixed with oil to a known weight of oil, brine and sand. Excess oil and/or brine were removed from the surface of each sandpack. The two sandpacks were then aged. The two sandpacks were prepared so as to be as similar as possible.

After ageing, one of the sandpacks was intended to be subjected to brine imbibition to produce oil therefrom, while the other was intended to be subjected to an MEOR process.

In a spontaneous imbibition experiment, the prepared and aged samples are merely soaked or submerged in a body of aqueous fluid, which is drawn into the sample by capillary action to displace oil. The imbibed fluid is at ambient pressure.

Initial NMR measurements of the $T_2$ distribution for the fluid within each aged sandpack were carried out.

FIG. 4-1 shows an experimental set-up, in which the two sandpacks, #110, 210 are housed each within a similar apparatus, the two apparatuses 1, 2 being positioned side by side.

The first set of apparatus 1 comprises a base 190 in threaded engagement with a vessel 120 and a sandpack 110, the sandpack 110 being located on the base 190 and within the vessel 120. Extending upwardly from the vessel 120 in a substantially vertical direction is an elongate tube 130, which tube 130 is in fluid communication with the internal volume of the vessel 120. The tube 130 is provided at its top end with a tap 140 for controlling the passage of fluid from the tube 130 to an opening 150 located beyond the tap 140. The tube 130 and vessel 120 are both made from glass. The tube 130 is provided on its outside with markings for assessing the amount or level of a fluid contained therein.

Also, extending outwardly from a side wall of the vessel 120 is an inlet tube 160 which provides fluid communication with the internal volume of the vessel 120. The inlet tube 160 is connected to a fluid supply line 170, which communicates with a source of fluid (not shown). The inlet tube 160 is provided with a tap 180 for controlling the flow of fluid from the fluid supply line 170 and into the vessel 120 through inlet tube 160.

The source of fluid comprises a container for a body of fluid. The fluid supply line 170 communicates with a lower portion of the container such that, in use, fluid is forced along the supply line 170 by the weight of the fluid in the container. In apparatus 1, the fluid comprises a simple brine solution.

The second set of apparatus 2 comprises a base 290 in threaded engagement with a vessel 220 and a sandpack 210, the sandpack 210 being located on the base 290 and within the vessel 220. Extending upwardly from the vessel 220 in a substantially vertical direction is an elongate tube 230, which tube 230 is in fluid communication with the internal volume of the vessel 220. The tube 230 is provided at its top end with a tap 240 for controlling the passage of fluid from the tube 230 to an opening 250 located beyond the tap 240. The tube 230 and vessel 220 are both made from glass. The tube 230 is provided on its outside with markings for assessing the amount or level of a fluid contained therein.

Also, extending outwardly from a side wall of the vessel 220 is an inlet tube 260 which provides fluid communication with the internal volume of the vessel 220. The inlet tube 260 is connected to a fluid supply line 270, which communicates with a source of fluid (not shown). The inlet tube 260 is provided with a tap 280 for controlling the flow of fluid from the fluid supply line 270 and into the vessel 220 through inlet tube 260. The source of fluid comprises a container for a body of fluid. The fluid supply line 270 communicates with a lower portion of the container such that, in use, fluid is forced along the supply line 270 by the weight of the fluid in the container. In apparatus 2, the fluid comprises a brine solution in which is dissolved two strains of microbes (a first strain that is capable of generating a biofilm and a second strain that is capable of modifying surface wetting properties of the sand).

Sandpacks 110 and 210 were prepared as described above. Accordingly, it will be appreciated that the sandpacks 110, 210 are aged prior to being included in the experimental apparatus. Hence, sandpacks 110, 210 contain a known volume of aqueous phase (brine) and oil phase (crude oil).

In the oil displacement experiment carried out in apparatus 1, taps 180 and 150 are initially open, as brine solution flows from the container into the vessel 120 via line 170. Once the resulting fluid level within tube 130 reaches a pre-determined height (typically close to the top of the marks on the outside of the tube 130), the taps 180, 150 are closed. Preferably, tap 180 is closed shortly before tap 150.

As the experiment progresses after the taps 180, 150 are closed, brine solution is imbibed into sandpack 110, thereby displacing crude oil. The volume of crude oil displaced is measured within the tube 130.

In the oil displacement experiment carried out in apparatus 2, taps 280 and 250 are initially open, with brine solution flowing from the container into the vessel 220 via line 270. Once the resulting fluid level within tube 230 reaches a pre-determined height (typically close to the top of the marks on the outside of the tube 230), the taps 280, 250 are closed. Preferably, tap 280 is closed shortly before tap 250.

As the experiment progresses after the taps 280, 250 are closed, brine solution is imbibed into sandpack 210, thereby displacing crude oil. The volume of crude oil displaced is measured within the tube 230.

It will be appreciated that the experiment carried out in apparatus 2 was exactly the same as that described above in respect of apparatus 1, except that the brine solution supplied along line 270 contained the two strains of microbes.

Differences in the volume of solution imbibed (oil displaced) and in the $T_2$ distribution profile between the two experiments may be attributed to the effects of the microbes on the interfacial activity, e.g. wettability, between the oil and the pore walls within the sandpack.

At the end of the oil displacement experiment, NMR $T_2$ relaxation time measurements were taken of the fluid remaining within the sandpacks (at residual oil saturation). The results for the two sandpacks were then compared.

Useful reference points for subsequent data analysis can be obtained by measuring $T_2$ relaxation time distributions for bulk samples of the oil and aqueous phases, a comparable porous sample which is 100% saturated with the aqueous phase and a comparable porous sample which is 100% saturated with the oil phase.

FIG. 4-2 shows the $T_2$ distributions (μs) for a number of samples, namely: (i) sandpack 110 at residual oil saturation after brine imbibition; (ii) sandpack 110 after ageing but before brine imbibition; (iii) a comparable sandpack sample 100% saturated with aqueous phase; (iv) a comparable sandpack sample 100% saturated with oil phase; and (v) a sample of bulk oil phase.

Samples (iii), (iv) and (v) represent useful points of reference for subsequent data analysis. Often, it will also be useful to obtain $T_2$ relaxation time data for a bulk sample of the aqueous phase.

The distribution curves do not lie on top of each other. In particular, it may be noted that the peak of the curve for brine imbibition occurs at a higher relaxation time than the peak of the curve for the sandpack after ageing and before brine imbibition. This is because the brine imbibition displaces oil from the sandpack.

FIG. 4-3 is similar to FIG. 4-2 but shows data from an MEOR experiment. Accordingly, FIG. 4-3 shows the $T_2$ distributions (μs) for the following samples: (i) sandpack 210 at residual oil saturation after MEOR imbibition; (ii) sandpack 210 after ageing but before MEOR imbibition; (iii) a comparable sandpack sample 100% saturated with aqueous phase; (iv) a comparable sandpack sample 100% saturated with oil phase; and (v) a sample of bulk oil phase.

Again, the distribution curves do not lie on top of each other. In particular, it may be noted that the peak of the curve for MEOR imbibition occurs at a higher relaxation time than the peak of the curve for the sandpack after ageing and before brine imbibition.

In FIG. 4-4, the $T_2$ distribution curves at residual oil saturation from FIGS. 4-2 and 4-3 are presented on the same axes. The residual oil saturation ($S_{or1}$) for the first sandpack 110 after brine imbibition was found to be 12.6% and the residual oil saturation ($S_{or2}$) for the second sandpack 210 after MEOR imbibition was found to be 8.1%. As can clearly be seen, the two curves do not lie on top of each other. The $T_2$ distributions for the first sandpack 110 after brine imbibition (i) and the second sandpack 210 after MEOR imbibition (ii) can therefore be compared. The curve for the MEOR imbibition experiment is shifted towards shorter relaxation times as compared with the curve for the brine imbibition experiment. In particular, the peak relaxation time for the MEOR experiment is shifted to a shorter time than that for the brine experiment. This may be owing to a stronger interaction between the water phase and the pore wall, i.e. increased wettability for the water phase. Thus, the MEOR imbibition process may have released at least a portion of the adhering oil that was not displaced by the brine imbibition process.

Figures 1, 2, 3, 4, 5:
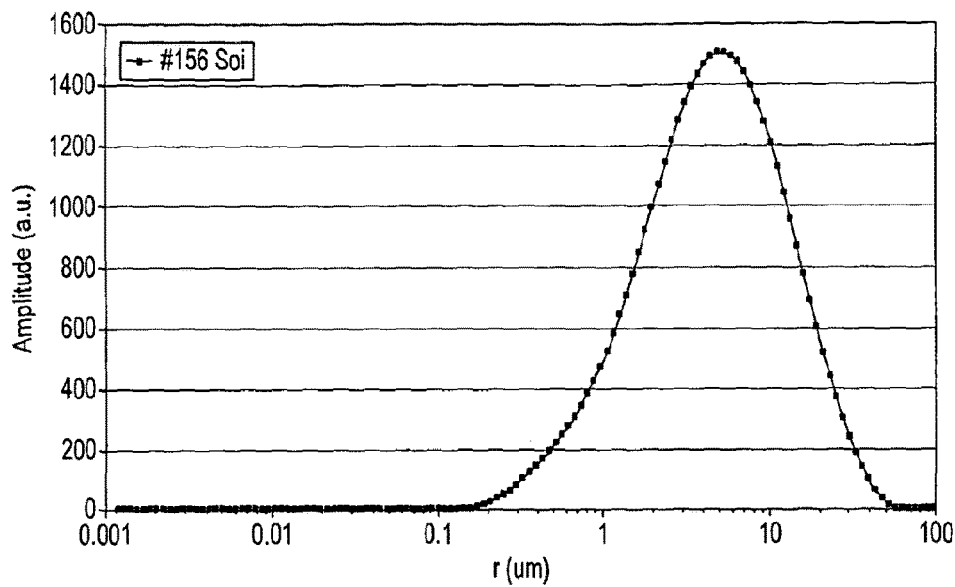

FIG. 4-5 serves to demonstrate the improved oil recovery that was achieved from sandpack 210 using the MEOR process (ii) as compared with from sandpack 110 via brine imbibition (i). FIG. 4-5 shows a quantity called the oil recovery factor plotted against time (t, (minutes)), the oil recovery factor being a measure of the proportion (expressed as a percentage) of the oil within the sandpack prior to imbibition (a known amount since the oil was added during sample preparation) that has been displaced from the sandpack during imbibition. The amount of oil displaced is measured by recording the volume of oil within the tubes 130 and 230 of apparatuses 1 and 2 respectively.

As can be seen, initially the rate of oil recovery from the sandpacks rose relatively quickly before flattening out to a much slower rate from around 500 minutes onwards. After the initial period during which the rate of oil recovery is relatively fast, the oil recovery factor for the MEOR experiment (sandpack 210) is consistently higher at any given time than for the brine experiment (sandpack 110). A reading taken after more than 8500 minutes recorded "final" oil recovery factors of 85.5% and 90.6% for brine imbibition (sandpack 110) and MEOR (sandpack 210) respectively.

Table 4-1 below shows the peak values from spin-spin relaxation time distributions at different saturation conditions for the brine imbibition process carried out on sandpack 110.

TABLE 4-1

| $T_{2B,W2}$ (ms) | $T_{2B,O}$ (ms) | $T_{2,W}$ (Sw = 1) (ms) | $T_{2,O}$ (So = 1) (ms) | $T_{2W}$ (Sor1) (ms) | Sw1 | $T_{2,O}$ (Soi) (ms) | Soi |
|---|---|---|---|---|---|---|---|
| 2297.8 | 68.335 | 113.532 | 54.974 | 113.532 | 0.874 | 59.109 | 0.869 |

$T_{2B,W2}$ is the peak relaxation time for a sample of bulk aqueous phase. $T_{2B,O}$ is the peak relaxation time for a sample of bulk oil phase. $T_{2,W(SW=1)}$ is the peak relaxation time for a comparable sandpack saturated with the aqueous phase. $T_{2,O(So=1)}$ is the peak relaxation time for a comparable sandpack saturated with the oil phase. $T_{2W(Sor1)}$ is the peak relaxation time measured after completion of the brine imbibition (oil displacement) experiment conducted on sandpack 110 in apparatus 1. $T_{2,O(Soi)}$ is the peak relaxation time measured after sandpack 110 was aged.

$S_{W1}$ is the final water saturation level within the sandpack 110 at the end of the oil displacement (brine imbibition) experiment conducted in apparatus 1. $S_{oi}$ is the initial oil saturation level in the aged sandpack 110.

$S_{W1}$ can be calculated from $S_{oi}$ and the oil recovery factor, since $S_{oi}$ is known for a given laboratory-prepared sample and the oil recovery factor is determined by experiment. For instance, consider a sandpack prepared such that $S_{oi}+S_{wi}=1$, where $S_{oi}=0.7$ and $S_{wi}=0.3$, which sandpack is then subjected to an oil recovery experiment which returns an oil recovery factor of 80%. In this case, the residual oil saturation level will be 0.14, i.e. 20% of $S_{oi}$, and the residual aqueous phase saturation level will be 0.86.

The values shown in Table 4-1 may be inserted into the equations set out above, in order to calculate the desired wettability indices.

For instance, by inputting the values into the wettability index calculation component, which executes steps according to equation (26a), the oil phase wettability index output by the wettability index calculation component (at initial the oil saturation condition for sandpack 110, $WI_{oi}$) is 0.56.

Similarly, if the wettability index calculation component is arranged to execute steps according to equation (32), it is calculated that the water phase wettability index (at residual oil saturation (Sor1) condition after the brine imbibition process, $WI_W$) is 0.87.

Table 4-2 below shows the equivalent data to Table 4-1, but in respect of the MEOR process carried out on sandpack 210.

TABLE 4-2

| $T_{2B,W2}$ (ms) | $T_{2B,O}$ (ms) | $T_{2,W}$ (Sw = 1) (ms) | $T_{2,O}$ (So = 1) (ms) | $T_{2W}$ (Sor2) (ms) | Sw2 | $T_{2,O}$ (Soi) (ms) | Soi |
|---|---|---|---|---|---|---|---|
| 2249.7 | 68.335 | 113.532 | 54.974 | 73.475 | 0.919 | 59.109 | 0.865 |

$T_{2B,W2}$ is the peak relaxation time for a sample of bulk aqueous phase. $T_{2B,O}$ is the peak relaxation time for a sample of bulk oil phase. $T_{2,W(SW=1)}$ is the peak relaxation time for a comparable sandpack saturated with the aqueous phase. $T_{2,O(So=1)}$ is the peak relaxation time for a comparable sandpack saturated with the oil phase. $T_{2W(Sor2)}$ is the peak relaxation time measured after completion of the brine imbibition (oil displacement) experiment conducted on sandpack 210 in apparatus 2. $T_{2,O(Soi)}$ is the peak relaxation time measured after sandpack 210 was aged.

$S_{W2}$ is the final water saturation level within the sandpack at the end of the oil displacement (MEOR) experiment conducted on sandpack 210 in apparatus 2. $S_{oi}$ is the initial oil saturation level in the aged sandpack 210. $S_{W2}$ may be calculated in a similar manner to $S_{W1}$.

The values shown in Table 4-2 may be inserted into the equations set out above, in order to calculate the desired wettability indices.

In accordance with equation (26a), the wettability index calculation component can calculate that the oil phase wettability index (at the initial oil saturation condition for sandpack 210, $WI_{oi}$) is 0.56. It is noted that this is the same value as for sandpack 110 which would suggest that the two sandpack samples were comparably similar, as desired, prior to undergoing brine imbibition or MEOR imbibition as the case may be.

If the wettability index calculation component is arranged to execute steps according to equation (33), it can be calculated that the water phase wettability index at residual oil saturation (Sor2) condition for sandpack 210 after the MEOR imbibition process is $WI_{W,EOR}$=1.45. This is a considerably higher value than for sandpack 110 after brine imbibition, which suggests that the porous medium (the sandpack) becomes relatively more water wet after the MEOR process, owing to the wettability modification effect of the MEOR process.

Using these values and Equation (34), it is possible for the wettability index modification factor calculation component to calculate the wettability index modification factor for the water phase owing to the MEOR process compared with brine imbibition as $WIMF_W$=1.66. This suggests that the MEOR process results in a very strong wettability modification to the water wetting state in comparison with the brine imbibition process.

A further sandpack experiment was performed as an additional control. Thus, a sandpack was prepared using the same produced sand that was used to prepare sandpacks 110, 210. The sand was 100% saturated with an inoculum (by being immersed in the inoculum). The inoculum was of identical composition to the brine solution containing the two strains of microbes that was used in the MEOR imbibition experiment for sandpack 210. After removal of excess inoculum, the sandpack was left to age for six days to allow a biofilm to grow on the surface of the sand. This ageing time corresponded to the period of time that sandpack 210 was subjected to MEOR imbibition (6 days). It should be noted that the sandpack employed in this control experiment was not exposed to crude oil. Owing to the absence of crude oil, there was no change to the surface coverage of the aqueous phase in the sandpack (i.e. the sandpack remained 100% saturated with inoculum).

Figures 1, 2, 3, 4, 5, 6:
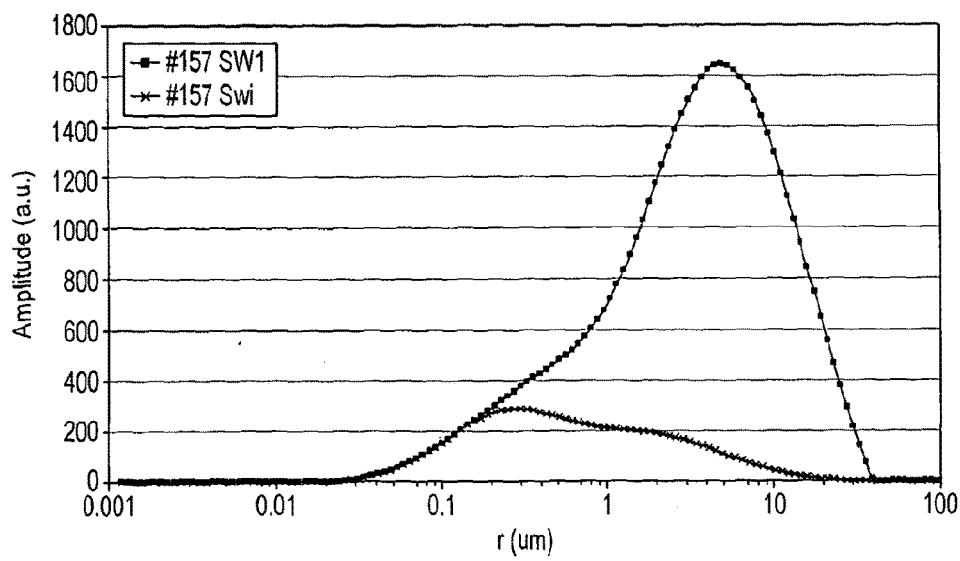
Figures 1, 2, 3, 4, 5, 6, 7:
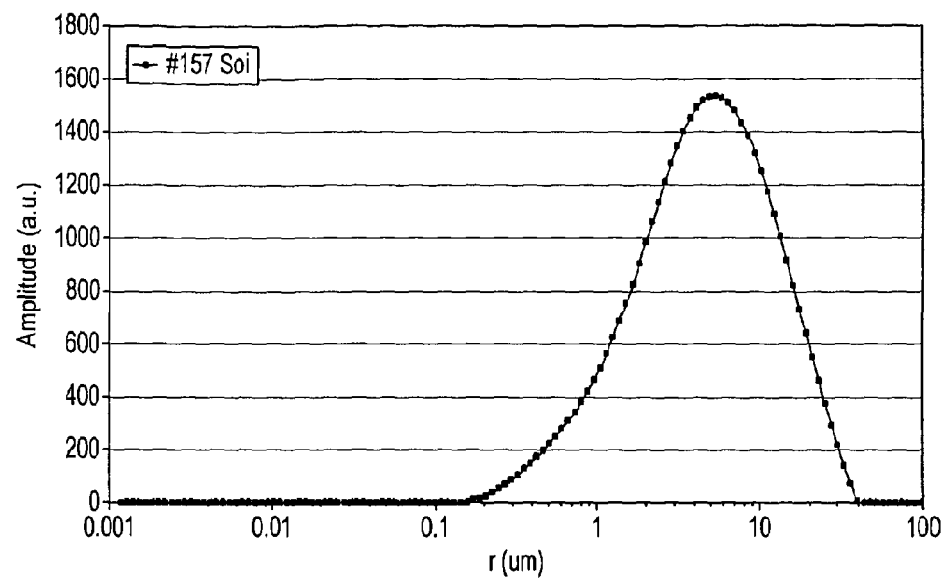
Figures 1, 2, 3, 4, 5, 6, 7, 8:
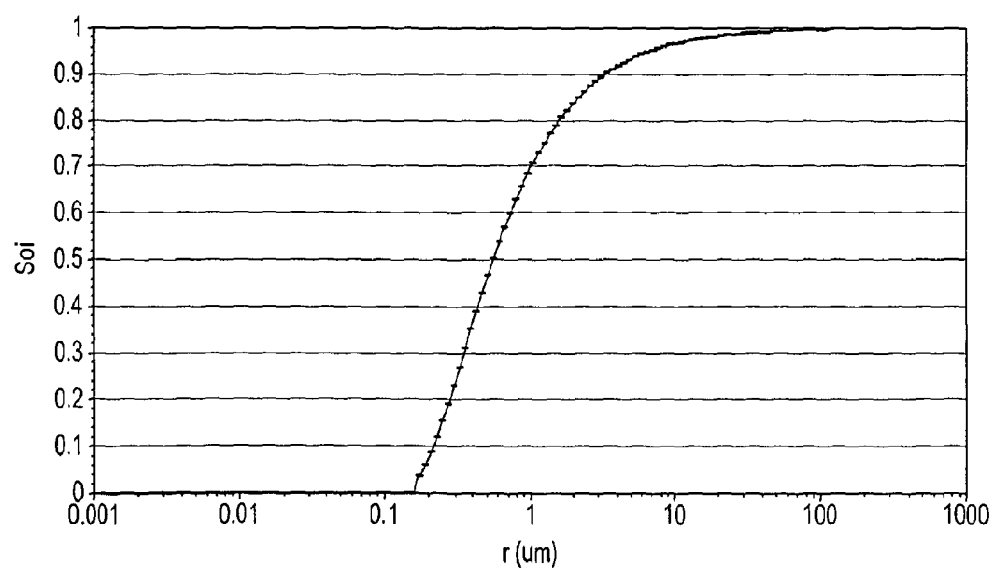
Figures 1, 2, 3, 4, 5, 6, 7, 8, 9:
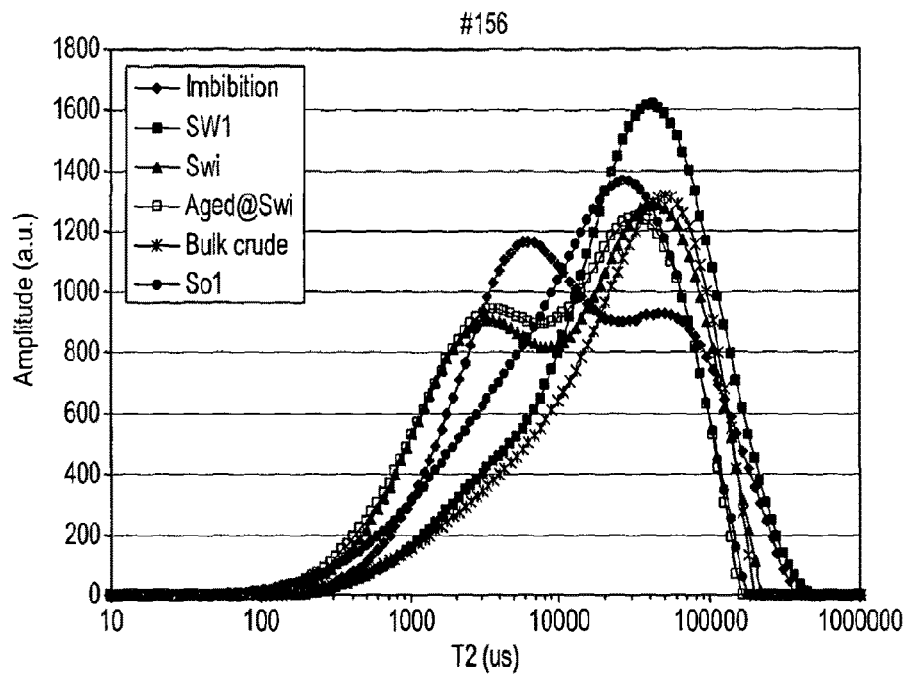
Figures 1, 2, 3, 4, 5, 6, 7, 8, 9, 10:
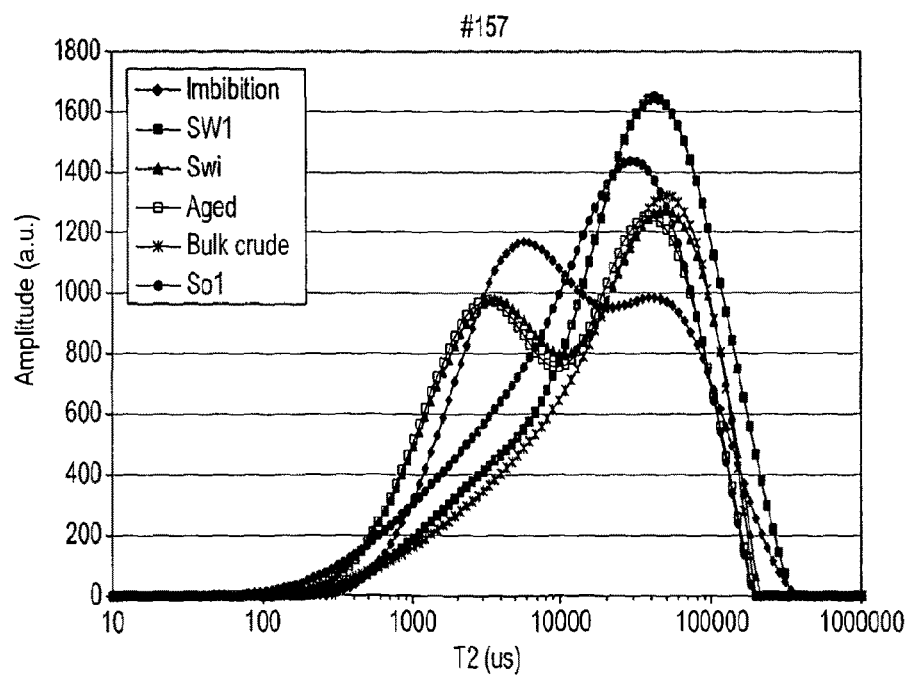
Figures 1, 2, 3, 4, 5, 6, 7, 8, 9, 10, 11:
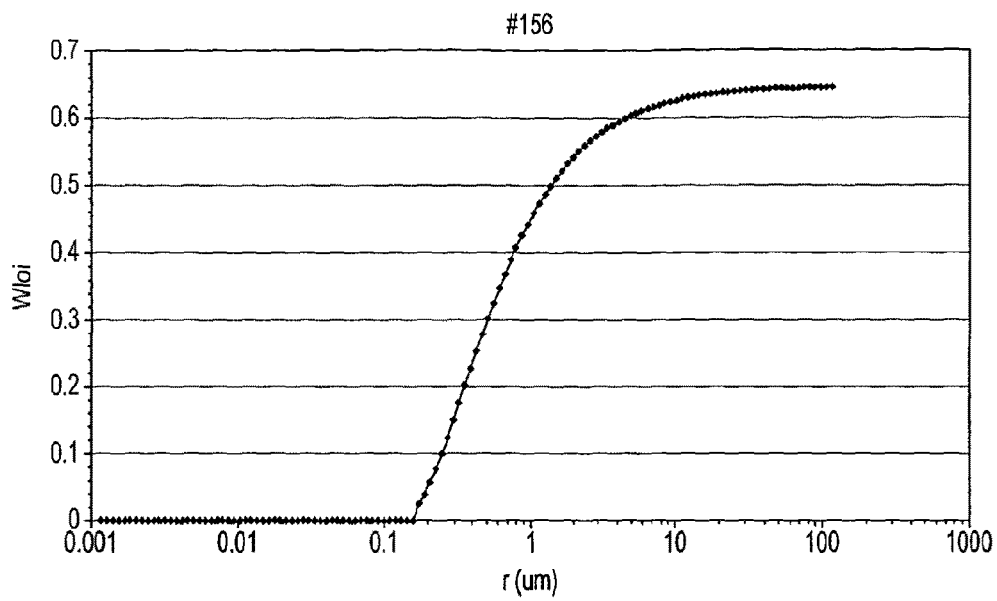
Figures 1, 2, 3, 4, 5, 6, 7, 8, 9, 10, 11, 12:
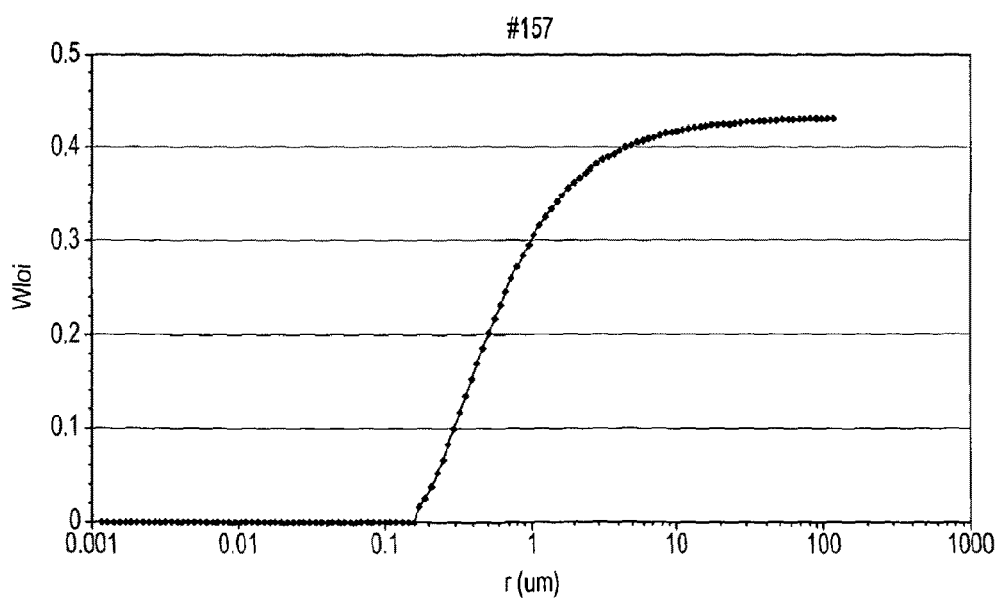
Figures 1, 2:
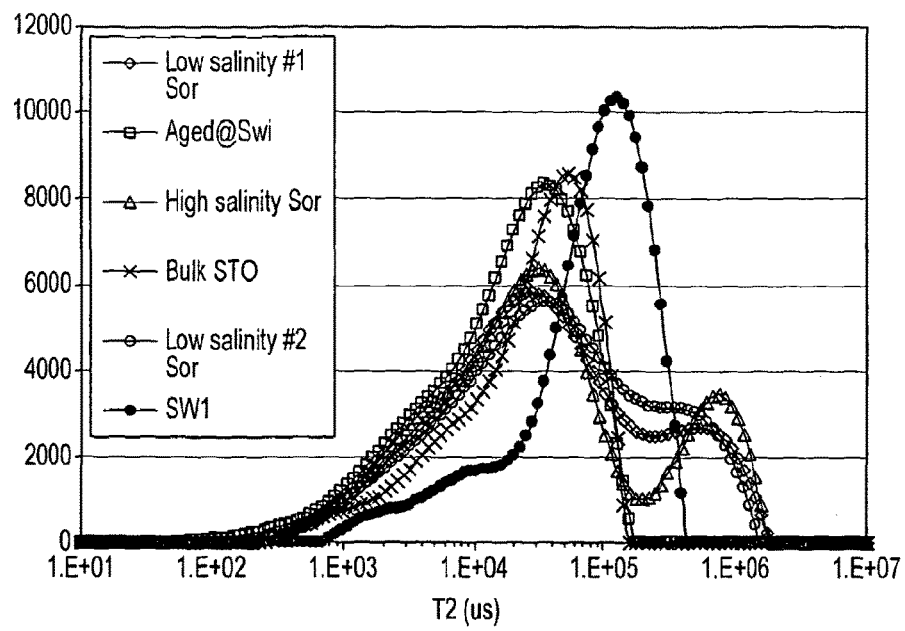
Figures 1, 3:
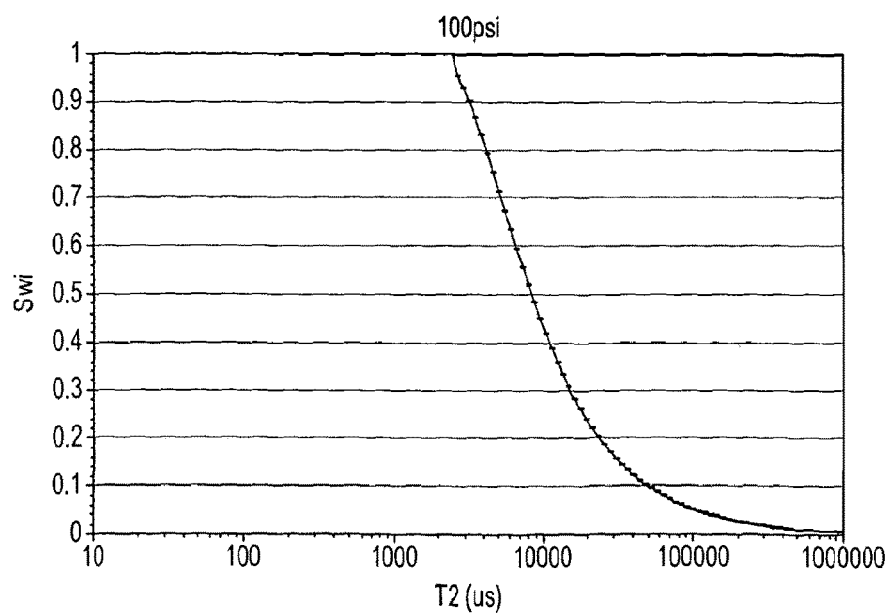
Figures 2, 3:
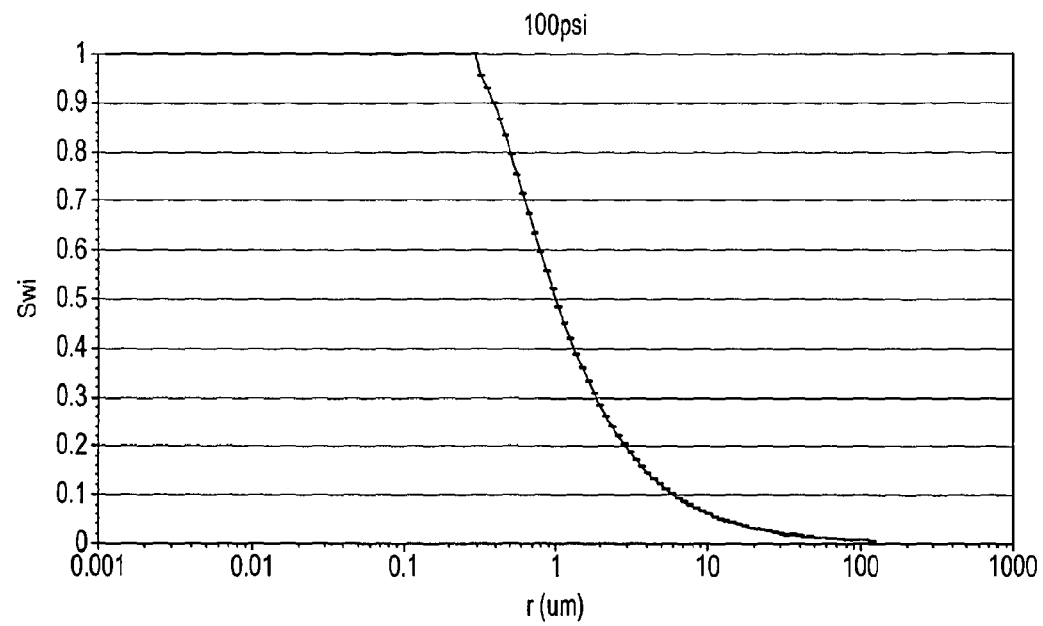
Figure 3:
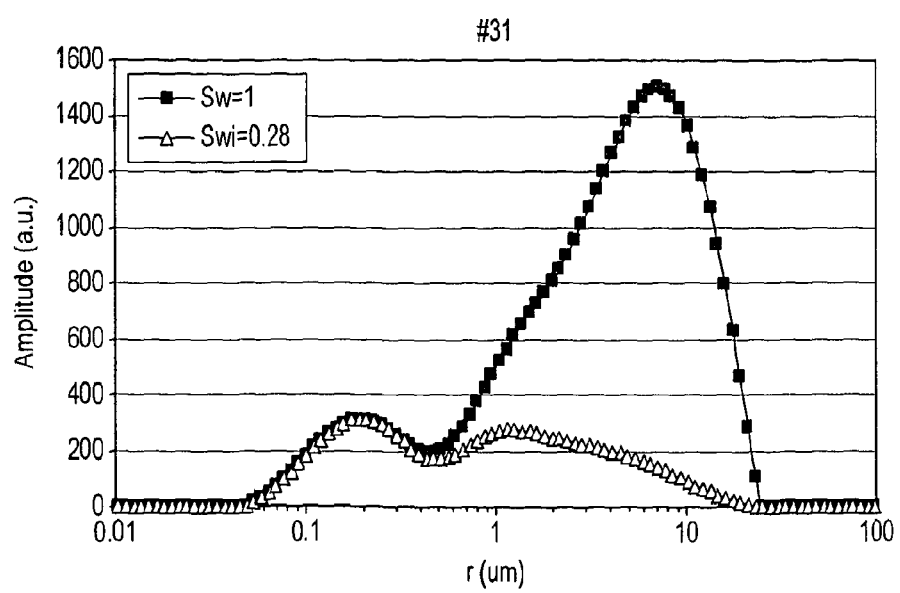
Figures 3, 4:
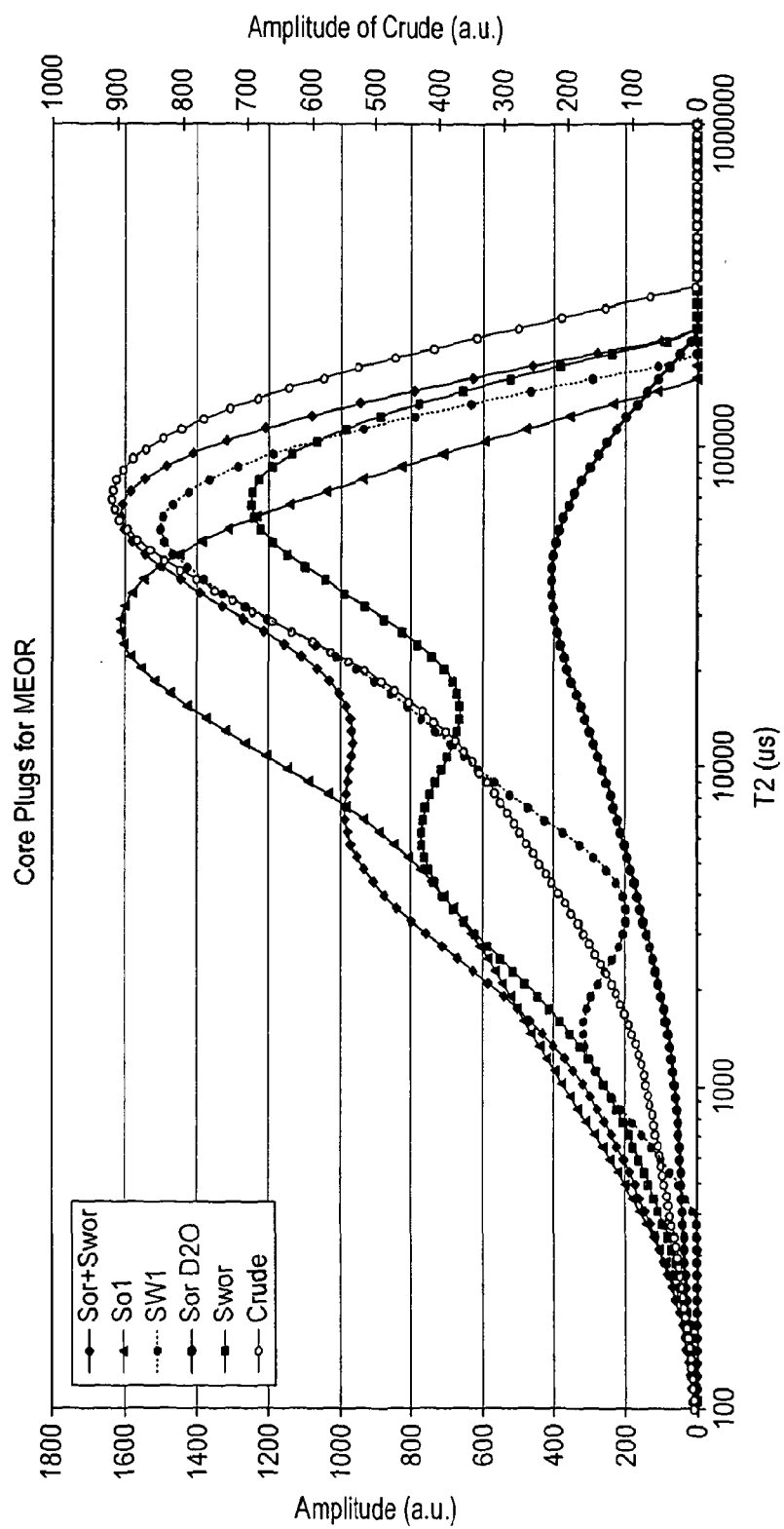
Figures 1, 4:
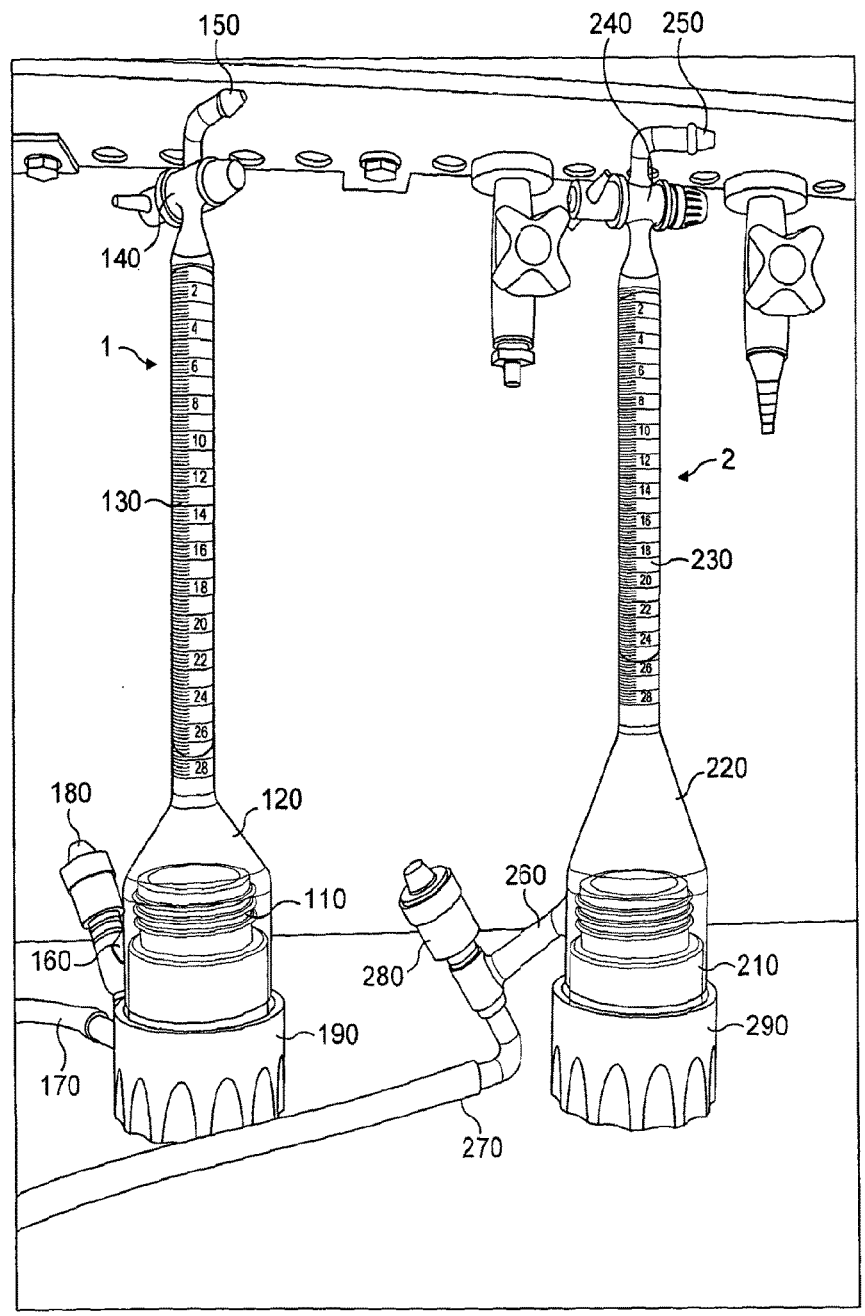
Figures 2, 4:
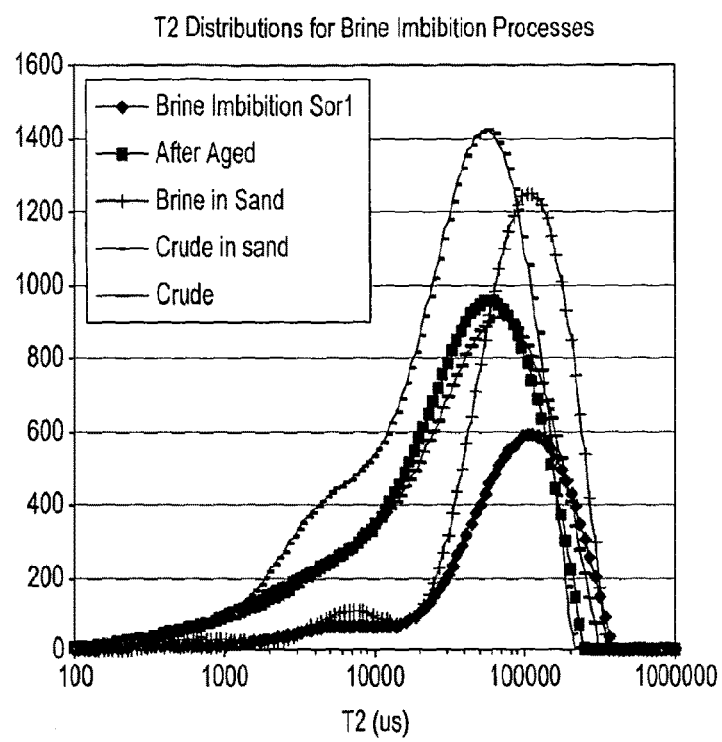
Figures 3, 4:
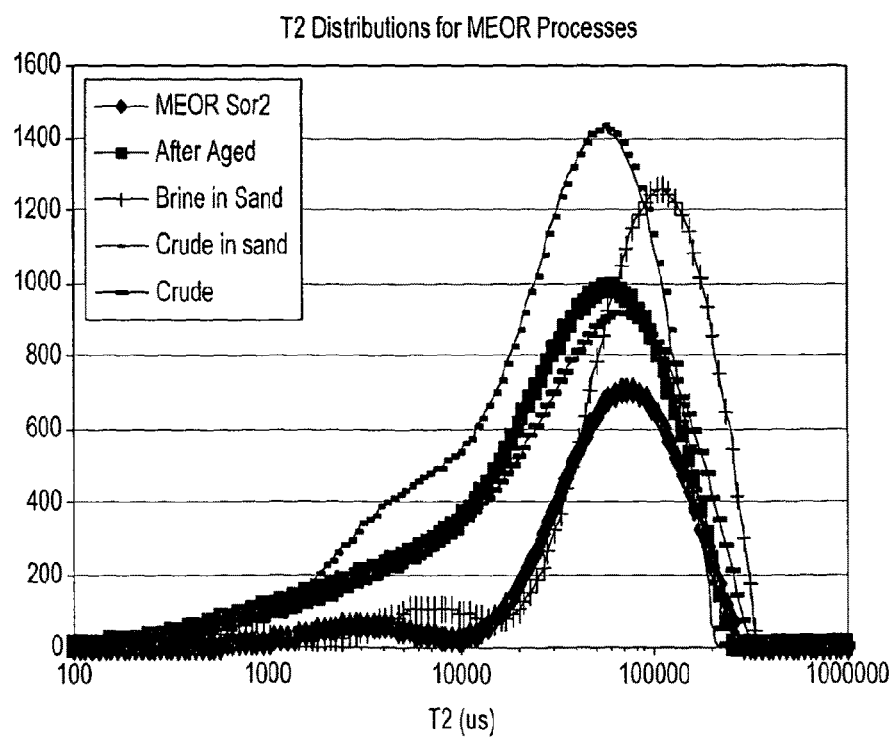
Figure 4:
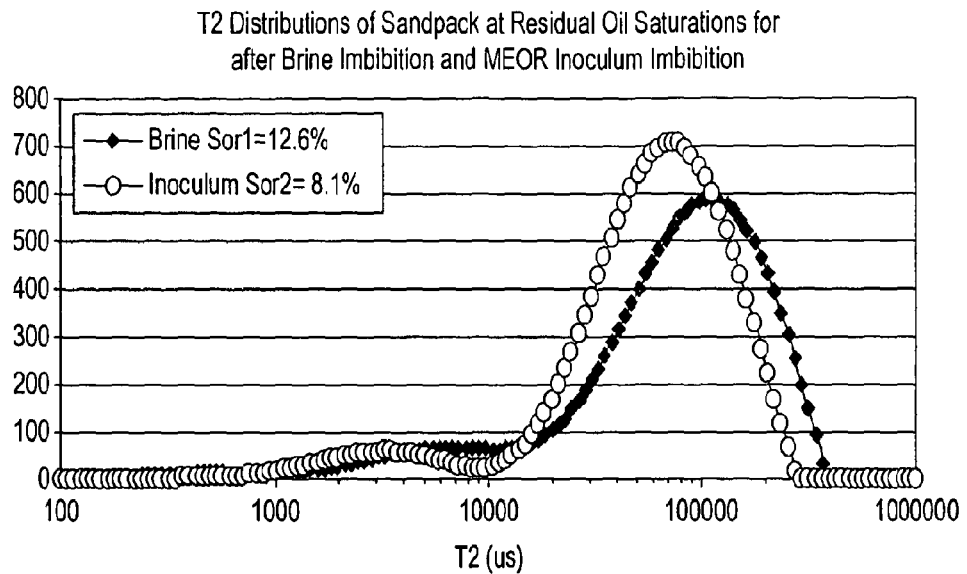
Figures 4, 5:
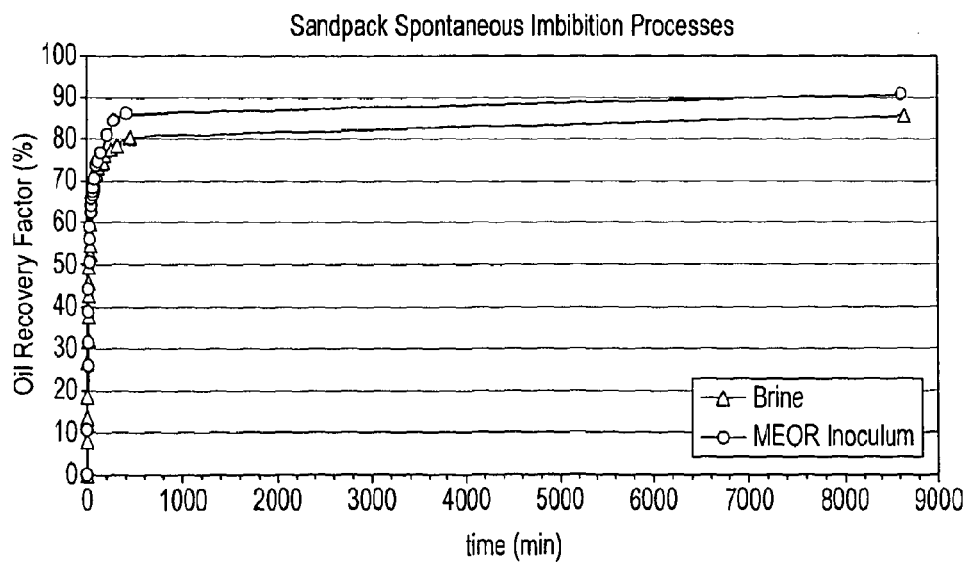
Figures 4, 5, 6:
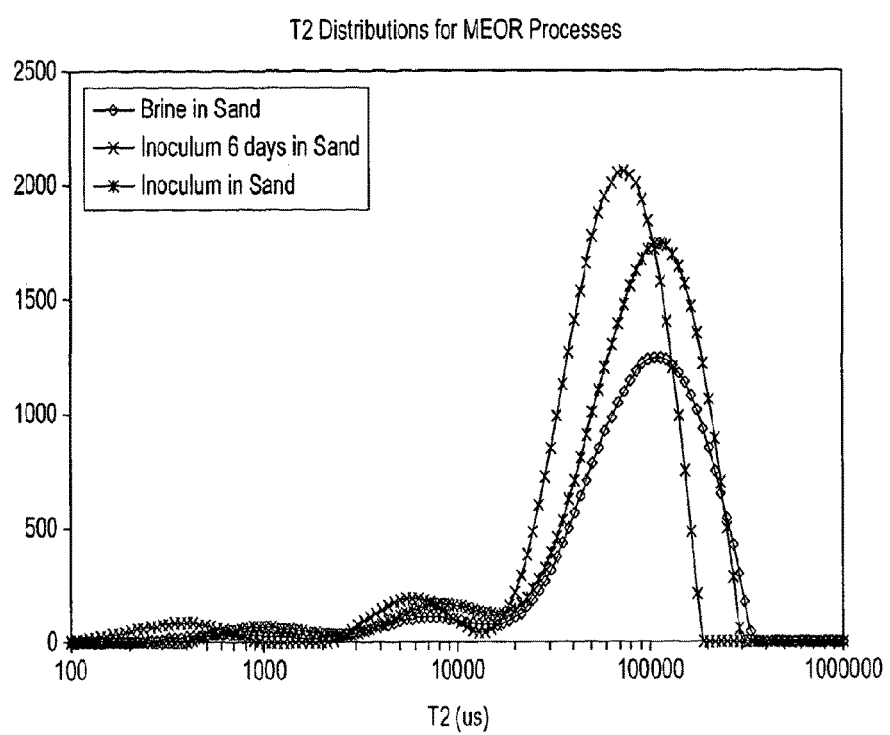
Figure 5:
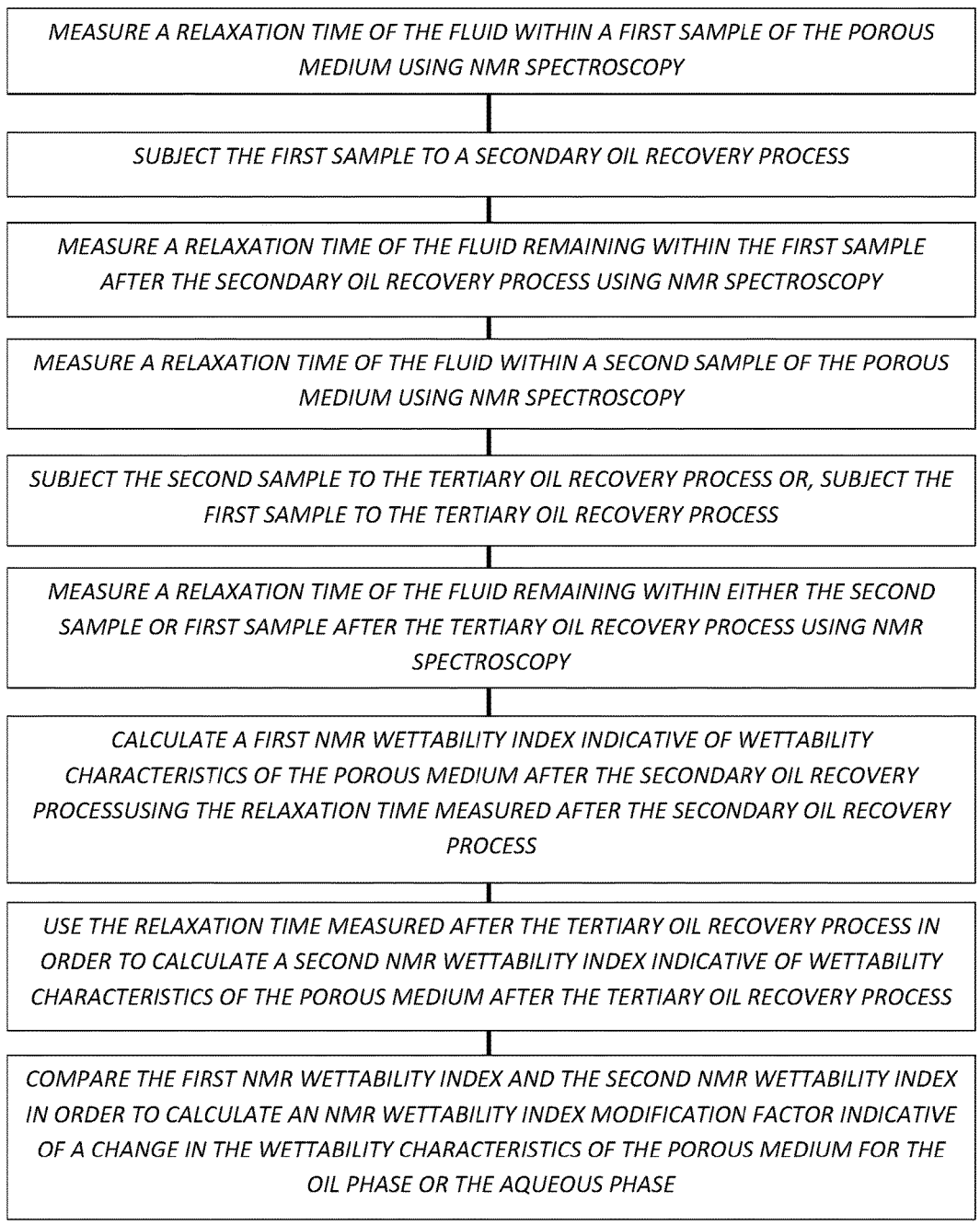
Figure 6:
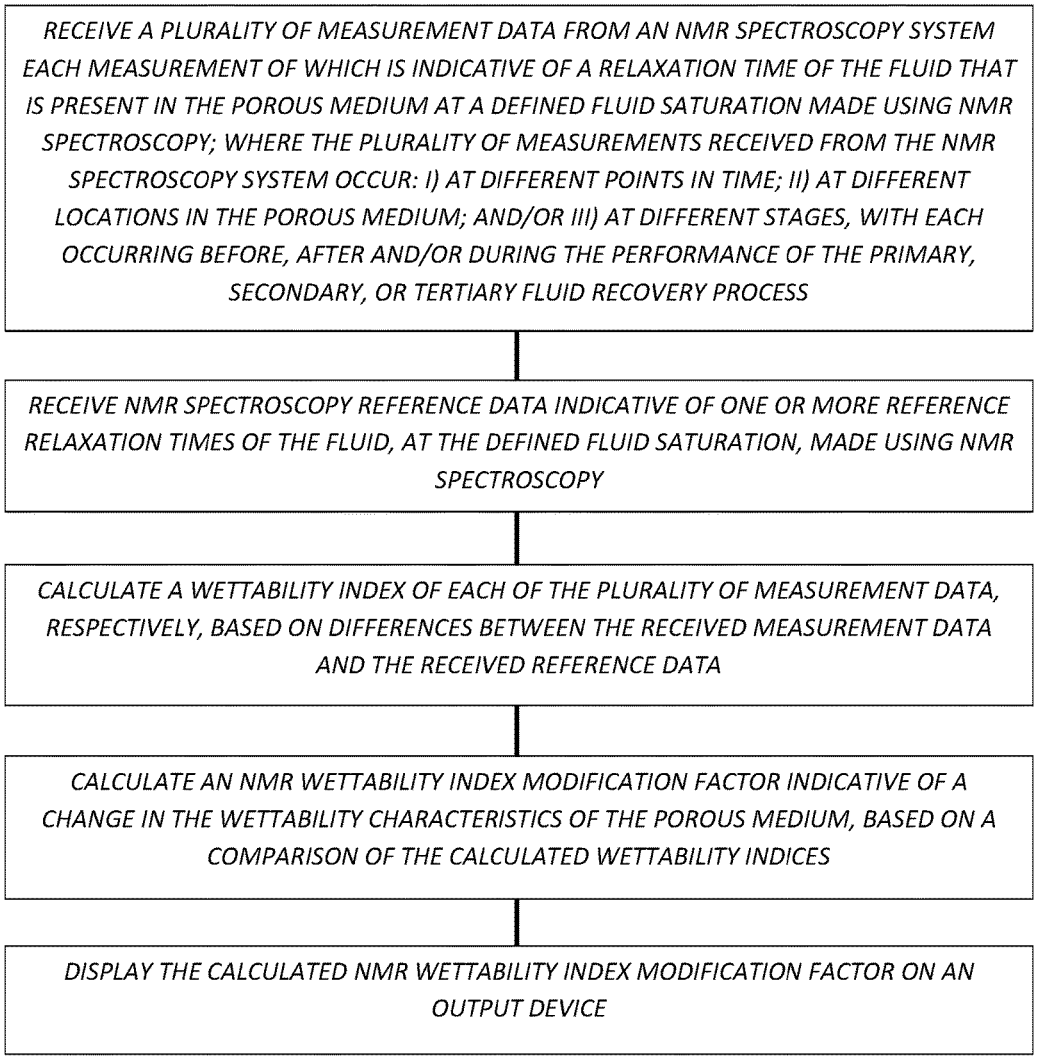

FIG. 4-6 shows the $T_2$ relaxation time distributions for (i) 100% brine saturated sandpack in the absence of microbes (taken from FIG. 4-3), (ii) 100% inoculum saturated sandpack before ageing and (iii) 100% inoculum saturated sand after ageing for 6 days. It can be seen that the $T_2$ relaxation time distribution of the 100% inoculum saturated sandpack before ageing is very similar to that for the 100% brine saturated sandpack. However, after 6 days ageing, the $T_2$ relaxation time distribution of the 100% inoculum saturated sandpack had shifted to the left hand side significantly. It is believed that the shift in the relaxation time distribution is caused by the growth of a biofilm (arising from the biofilm generating strain of microbes). This generated biofilm (typically comprising biopolymers) adheres to the sand grain surface, which reduces the mobility of water phase, thereby reducing $T_2$ relaxation times (the biofilm allows the water phase to adhere more strongly to the sand particles). The results also show that NMR $T_2$ relaxation time distribution measurements can be used for monitoring biofilm growth in porous media non-intrusively.

As discussed above, based on the peak $T_2$ relaxation time value for sandpack 210 when 100% saturated with brine (at Sw=1), the calculated water phase wettability index (at residual oil saturation after the MEOR process, $WI_{W,EOR}$) was found to be 1.45. This wettability index therefore accounts for both a surface coverage modification effect by the strain of surface modification microbes and a surface affinity modification effect by the strain of biofilm generating microbes.

Table 4-3 is similar to Table 4-2 in that it shows the peak values of $T_2$ relaxation time distributions at different saturation conditions during the MEOR imbibition process for sandpack 210. However, in Table 4-3, the peak $T_2$ relaxation time value for 100% inoculum saturated sandpack after aging for 6 days (73.475 ms) is used for the 100% water phase saturated state (Sw=1). When this datum is applied to calculate the wettability index for sandpack 210, the surface affinity modification effect due to the generated biofilm can be cancelled out as the shift in peak $T_2$ relaxation time value for 100% inoculum saturated sandpack after ageing can only arise as a result of the growth of biofilm on the sandpack. Using equation (33) and the data in Table 4-3, the water phase wettability index (at residual oil saturation (Sor2) condition after the MEOR process for sandpack 210, $WI_{W,EOR}$) calculated by the wettability index calculation component is 0.92. This wettability index therefore only takes into account the surface coverage modification effect arising from the strain of microbes that modifies surface wetting (interfacial) properties. The strain of microbes that changes surface wetting or interfacial properties of the sand may release oil from the sand and thereby reduce the surface coverage of the oil phase and increase the surface coverage of the water phase.

TABLE 4-3

| $T_{2B,W2}$ (ms) | $T_{2B,O}$ (ms) | $T_{2,W}$ (Sw = 1) (ms) | $T_{2,O}$ (So = 1) (ms) | $T_{2W}$ (Sor2) (ms) | Sw2 | $T_{2,O}$ (Soi) (ms) | Soi |
|---|---|---|---|---|---|---|---|
| 2249.7 | 68.335 | 73.475 | 54.974 | 73.475 | 0.919 | 59.109 | 0.865 |

It will be appreciated that the NMR techniques according to this invention may be used to confirm or determine the relative effectiveness of oil recovery processes, in particular tertiary mode oil recovery processes, for particular reservoir rock types. As a consequence, it may be possible to select an optimum or most appropriate oil recovery process for a given reservoir.

While the preceding examples demonstrate the application of the methods of the invention within the laboratory, it is envisaged that the methods would also be usefully applicable outside the laboratory, e.g. in an oil field, where the measurement of wettability and/or changes therein would be desirable.

For instance, experiments could be carried out in the field in which downhole NMR logging may be used to obtain wettability data in the region of a hydrocarbon-bearing formation around a wellbore. NMR data for the bulk water phase may be obtained in the field using downhole NMR logging of an underlying aquifer that is in hydraulic communication with the hydrocarbon-bearing formation. NMR data for the bulk oil phase may be obtained using a sample of crude that has been produced from the hydrocarbon-bearing formation.

It may be necessary to work out the original oil saturation as a base for calculating an estimate of the amount of oil in place within a formation. Also, a saturation profile may be required.

It is envisaged that it would also be possible to assess the extent of any changes in the wettability characteristics of and/or damage to a given formation that may be caused by the drilling process using NMR.

During drilling of a well, a wellbore will typically be full of drilling fluid (also known as drilling mud). The drilling fluid may seep out of the wellbore and into the near wellbore region of the formation, which may in turn displace oil away from the wellbore.

Hence, it will be appreciated that the saturation conditions within the near wellbore region of the formation will vary with distance from the wellbore as a consequence of the infiltration of drilling fluid into the formation. For instance, owing to the infiltration of drilling fluid into the formation, the rock proximal to the wellbore may no longer have the original oil saturation level of the formation. By measuring the wettability characteristics of the near wellbore region using an NMR logging tool, it may be possible to determine the extent of the infiltration of the drilling mud by ascertaining at what distance from the wellbore, the rock has the original oil saturation level.

Hence, changes in wettability in the near wellbore area owing to the presence within the formation of drilling fluid can be compared.

Using an oil-based drilling mud with a surfactant may change the wettability conditions of the formation. Accordingly, it will be appreciated that the techniques of the present invention may be used to assess and/or compare the effects of different drilling fluids or muds on the wettability characteristics of the near wellbore region of a formation.

Similarly, comparative wettability tests could be carried out after a secondary mode oil recovery process, e.g. water (or brine) flood or a tertiary mode oil recovery process such as MEOR.

Also, it should be noted that NMR logging may be carried out in injection wells and/or production wells. In the case of an injection well, for instance, NMR logging may be used to measure relaxation times for the fluid in the near wellbore region. Hence, it is envisaged that it may be possible to ascertain how much oil has been left behind within the near wellbore region of the formation, e.g. after a water flood or EOR process.

It will be appreciated that proton ($^1$H) NMR may be particularly well suited for studies of porous media containing therein fluids comprising water and hydrocarbon phases. However, it is anticipated that other modes of NMR may be useful for investigating other mixed phase fluid systems in porous media and that the principles of this invention may be applicable when using such other modes of NMR spectroscopy.

The invention claimed is:

1. A method of comparing a secondary oil recovery process with a tertiary oil recovery process using NMR spectroscopy, the secondary oil recovery process and the tertiary oil recovery process being applied to a substantially fluid-saturated porous medium containing an oil phase and an aqueous phase, the method comprising:
   (a) measuring a relaxation time of the fluid within a first sample of the porous medium using NMR spectroscopy, the first sample having pores and within the pores there is a known initial volume of the oil phase;
   (b) subjecting the first sample to the secondary oil recovery process;
   (c) measuring a relaxation time of the fluid remaining within the first sample after the secondary oil recovery process using NMR spectroscopy;
   (d) measuring a relaxation time of the fluid within a second sample of the porous medium using NMR spectroscopy, the second sample also having pores and within the pores thereof a substantially similar known initial volume of the oil phase;
   (e) subjecting the second sample to the tertiary oil recovery process or, subsequent to step (d) and without carrying out steps (e) and (f), subjecting the first sample to the tertiary oil recovery process;
   (f) measuring a relaxation time of the fluid remaining within either the second sample or first sample after the tertiary oil recovery process using NMR spectroscopy;
   (g) using the relaxation time measured after the secondary oil recovery in order process in order to calculate a first NMR wettability index indicative of wettability characteristics of the porous medium after the secondary oil recovery process;
   (h) using the relaxation time measured after the tertiary oil recovery process in order to calculate a second NMR wettability index indicative of wettability characteristics of the porous medium after the tertiary oil recovery process; and
   (i) comparing the first NMR wettability index and the second NMR wettability index in order to calculate an NMR wettability index modification factor indicative of a change in the wettability characteristics of the porous medium for the oil phase or the aqueous phase, thereby setting forth a comparison of the effects of the tertiary oil recovery process on the porous medium with those of the secondary oil recovery process.

2. A method as claimed in claim 1 wherein the relaxation time measurements are made with respect to the oil phase and/or the aqueous phase.

3. A method as claimed in claim 1 wherein the substantially fluid saturated porous medium is a reservoir rock, or a replica thereof, and contains an oil phase selected from: a live crude oil and a stock tank crude oil that is associated with the reservoir rock; and an aqueous phase selected from: a connate water and a formation water that is associated with the reservoir rock.

4. A method as claimed in claim 1 wherein the secondary oil recovery process comprises a waterflood and/or brine imbibition that utilizes a brine solution selected from seawater, brackish water, an aquifer water, a produced water, a connate water, a formation water and laboratory-prepared replicas/models thereof.

5. A method as claimed in claim 4 wherein the brine solution contains a microbe selected from; bacillus, clostridia, pseudomonas, hydrocarbon degrading bacteria, and denitrifying bacteria.

6. A method as claimed in claim 4 wherein the brine solution is a low salinity water having a total dissolved solids content in a range of 500 to 5000 ppm and a ratio of a multivalent cation content of the low salinity water to a multivalent cation content of the connate water, or formation water, of less than 1, preferably, less than 0.9.

7. A method as claimed in claim 1 wherein the relaxation time measurements are spin-spin (transverse) relaxation time measurements ($T_2$) made using NMR spectroscopy.

8. A method as claimed in claim 1 wherein the measurements are normalized with a processor by reference to the relaxation time measurements made using NMR spectroscopy on a sample of the porous medium that is saturated with a single water phase, and/or on a sample of the porous medium that is saturated with a single oil phase and/or on bulk samples of the aqueous phase and/or the oil phase.

9. An NMR spectroscopy computer-implemented method that when executed by a processor determines wettability characteristics of a fluid-bearing porous medium, in primary, secondary, or tertiary fluid recovery processes, the method comprising the steps of:
   receiving a plurality of measurement data from an NMR spectroscopy system each measurement of which is indicative of a relaxation time of the fluid that is present in the porous medium at a defined fluid saturation made using NMR spectroscopy with the plurality of measurements being received from the NMR spectroscopy system occurring:
   i) at different points in time;
   ii) at different locations in the porous medium; and/or
   iii) at different stages, wherein each of i), ii), and/or iii) occur before, after and/or during the performance of the primary, secondary, or tertiary fluid recovery process;
   receiving NMR spectroscopy reference data, from a database comprising non-transitory computer readable media, indicative of one or more reference relaxation times of the fluid, at the defined fluid saturation, made using NMR spectroscopy;
   calculating, with a central processing unit, a wettability index of each of the plurality of measurement data, respectively, based on differences between the received measurement data and the received reference data, each said calculated wettability index being indicative of the wettability characteristics of the porous medium at the defined fluid saturation;
   calculating, with a central processing unit, an NMR wettability index modification factor indicative of a change in the wettability characteristics of the porous medium, based on a comparison of the calculated wettability indices; and
   displaying, the calculated NMR wettability index modification factor on an output device;
   an NMR wettability index modification factor that is indicative of a change in the wettability characteristics of the porous medium based on a comparison of the calculated wettability indices; and
   an output device arranged in order to display the calculated NMR wettability index modification factor.

10. A method according to claim 9, further comprising the step of receiving from the NMR spectroscopy system data indicative of parameters relating to pore size, capillary pressure, fluid saturation of the porous medium and/or a height above free water level in the porous medium, in order to calculate the wettability index as a function of these parameters with the central processing unit.

11. A method according to claim 9, wherein said different locations in the porous medium relate to first and second wellbores arranged in order to penetrate the porous medium, the wettability index modification factor that is calculated being indicative of a change between the wettability characteristics of the porous medium at said different locations in the first and second wellbores.

12. A method according to claim 10, wherein said different locations in the porous medium relate to first and second wellbores arranged in order to penetrate the porous medium, the wettability index modification factor that is calculated being indicative of a change between the wettability characteristics of the porous medium at said different locations in the first and second wellbores.

13. A method according to claim 9, wherein the fluid present in the porous medium comprises at least two immiscible fluid components or immiscible fluid phases, and wherein the wettability index is calculated for at least one of said immiscible fluid components or immiscible fluid phases.

14. A method according to claim 9, wherein the received NMR spectroscopy reference data from the database comprises relaxation time measurements made, using NMR Spectroscopy, on:
   i) a sample of the porous medium that is saturated with a single aqueous phase;
   ii) a sample of the porous medium that is saturated with a single oil phase; and/or
   iii) bulk samples of an aqueous phase and/or an oil phase corresponding to that of the porous medium.

15. A method according to claim 9, comprising normalizing the received relaxation time measurement data based on the received NMR spectroscopy reference data from the database.

16. A method according to claim 14, wherein the received relaxation time measurements are spin-spin (transverse) relaxation time measurements made using NMR spectroscopy.

17. A method according to claim 9, wherein the porous medium comprises a reservoir rock formation, a sample of the reservoir rock formation or a replica of the reservoir rock formation.

18. A NMR spectroscopy system configured for determining wettability characteristics of a fluid-bearing porous medium, in primary, secondary, or tertiary fluid recovery processes, the system comprising:
   a data receiving means arranged in order to receive from an NMR spectroscopy system a plurality of measurement data, each measurement of which is indicative of a relaxation time of said fluid present in the porous medium, at a defined fluid saturation made using NMR spectroscopy; with the plurality of measurements being received from the NMR spectroscopy system data receiving means:
i) at different points in time;
ii) at different locations in the porous medium; and/or
iii) at different stages, wherein each of the i), ii), and/or iii) occur before, after and/or during the performance of the primary, secondary or tertiary fluid recovery process;
a data receiving means arranged in order to receive, from a database comprising non-transitory computer readable media, a plurality of NMR spectroscopy reference data that is indicative of one or more reference relaxation times of the fluid made using NMR spectroscopy;
a computer-implemented means arranged in order to calculate a wettability index with respect to each of the plurality of received measurement data found in (i), (ii), and/or (iii) respectively, based on differences between the received measurement data and the corresponding received reference data from the database, said wettability index being indicative of the wettability characteristics of the porous medium at the defined fluid saturation;
a computer-implemented means arranged in order to calculate an NMR wettability index modification factor that is indicative of a change in the wettability characteristics of the porous medium based on a comparison of the calculated wettability indices; and
an output device arranged in order to display the calculated NMR wettability index modification factor.

* * * * *